(12) United States Patent
Ierulli

(10) Patent No.: US 9,364,367 B2
(45) Date of Patent: Jun. 14, 2016

(54) OVERLAPPING RESILIENT MEMBER STRUCTURES IN NASAL DILATOR DEVICES

(75) Inventor: Joseph V. Ierulli, Portland, OR (US)

(73) Assignee: Corbett Lair, Inc., Vancouver, WA (US)

( * ) Notice: Subject to any disclaimer, the term of this patent is extended or adjusted under 35 U.S.C. 154(b) by 274 days.

(21) Appl. No.: 13/286,838

(22) Filed: Nov. 1, 2011

(65) Prior Publication Data
US 2013/0104882 A1  May 2, 2013

(51) Int. Cl.
*A61M 29/00* (2006.01)
*A61F 5/08* (2006.01)

(52) U.S. Cl.
CPC ............. *A61F 5/08* (2013.01); *Y10T 29/49826* (2015.01)

(58) Field of Classification Search
CPC .................................. A61F 5/08; A61M 29/00
USPC .......... 606/204.45, 199; 128/200.24; 602/5, 6
See application file for complete search history.

(56) References Cited

U.S. PATENT DOCUMENTS

| | | |
|---|---|---|
| 5,476,091 A | 12/1995 | Johnson |
| 5,479,944 A | 1/1996 | Petruson |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| RE35,408 E | 12/1996 | Petruson |
| 5,611,333 A | 3/1997 | Johnson |
| 5,653,224 A | 8/1997 | Johnson |
| 5,706,800 A | 1/1998 | Cronk et al. |
| 5,718,224 A | 2/1998 | Muchin |
| 5,769,089 A | 6/1998 | Hand et al. |
| 5,890,486 A | 4/1999 | Mitra et al. |
| 5,931,854 A | 8/1999 | Dillon |
| 5,957,126 A | 9/1999 | Neeser |
| 6,006,746 A | 12/1999 | Karell |
| 6,029,658 A | 2/2000 | De Voss |
| 6,058,931 A | 5/2000 | Muchin |
| 6,065,470 A | 5/2000 | Van Cromvoirt et al. |
| 6,098,616 A | 8/2000 | Lundy et al. |
| 6,196,228 B1 | 3/2001 | Kreitzer et al. |
| 6,244,265 B1 | 6/2001 | Cronk et al. |
| 6,276,360 B1 | 8/2001 | Cronk et al. |
| 6,318,362 B1 | 11/2001 | Johnson |
| 6,352,548 B1 * | 3/2002 | Blach et al. ................... 606/199 |
| 6,357,436 B1 | 3/2002 | Kreitzer et al. |
| 6,375,667 B1 * | 4/2002 | Ruch ............................. 606/199 |
| 6,453,901 B1 | 9/2002 | Ierulli |
| 6,470,883 B1 | 10/2002 | Beaudry |
| 6,550,474 B1 | 4/2003 | Anderson et al. |
| 6,694,970 B2 | 2/2004 | Spinelli et al. |
| 6,769,428 B2 | 8/2004 | Cronk et al. |
| 6,769,429 B1 | 8/2004 | Benetti |
| 7,067,710 B1 | 6/2006 | Beaudry |

(Continued)

OTHER PUBLICATIONS

Written Opinion of the International Searching Authority dated Feb. 28, 2013 re: PCT/US2012/062331 filed Oct. 27, 2012.

*Primary Examiner* — Katherine Rodjom
(74) *Attorney, Agent, or Firm* — Mersenne Law

(57) ABSTRACT

A nasal dilator is constructed as a single body truss having a resilient member structure comprising a plurality of overlaid, island-placed, or overlapping resilient members. Methods of mass producing dilator devices, individual resilient members, and overlapped, overlaid, and island-placed resilient member structures are also disclosed.

20 Claims, 20 Drawing Sheets

(56) References Cited

U.S. PATENT DOCUMENTS

| | | |
|---|---|---|
| 7,114,495 B2 | 10/2006 | Lockwood, Jr. |
| D639,762 S | 6/2011 | Brogden et al. |
| D644,324 S | 8/2011 | Brunner et al. |
| D644,325 S | 8/2011 | Brunner et al. |
| 2003/0000521 A1* | 1/2003 | Beaudry .................. 128/200.24 |
| 2007/0255309 A1* | 11/2007 | Guyuron .................. A61F 5/08 606/199 |
| 2008/0097517 A1 | 4/2008 | Holmes et al. |
| 2008/0257341 A1* | 10/2008 | Ierulli ...................... 128/200.24 |
| 2009/0020115 A1 | 1/2009 | Lockwood, Jr. |
| 2009/0048626 A1 | 2/2009 | Beaudry |
| 2009/0125052 A1 | 5/2009 | Pinna et al. |
| 2010/0210988 A1* | 8/2010 | Dallison et al. ................. 602/61 |
| 2010/0298861 A1 | 11/2010 | Fenton |
| 2011/0000483 A1 | 1/2011 | Matthias et al. |
| 2011/0054517 A1 | 3/2011 | Holmes et al. |

\* cited by examiner

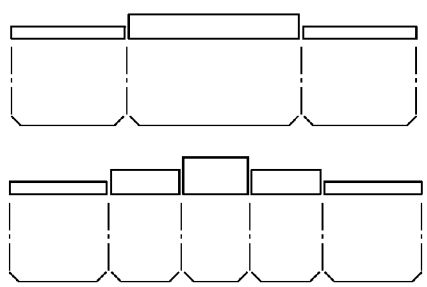
FIG. 3
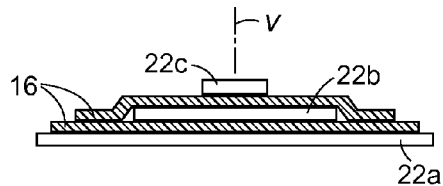
FIG. 2c
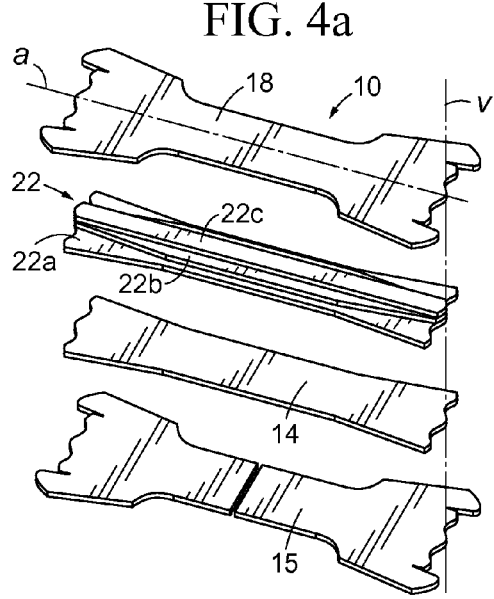
FIG. 4a
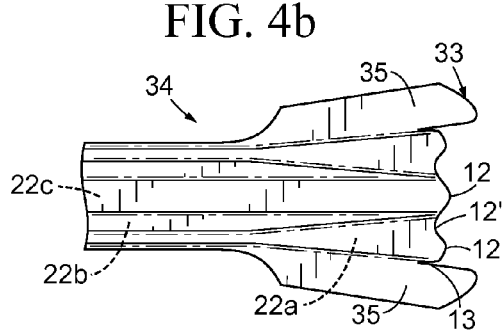
FIG. 4b
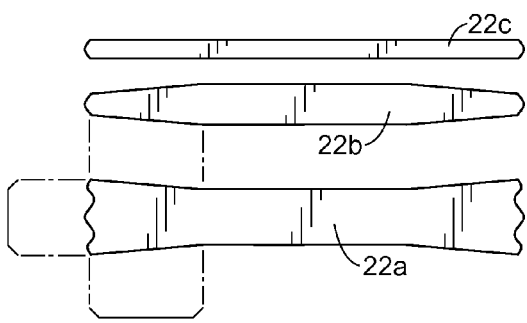
FIG. 5
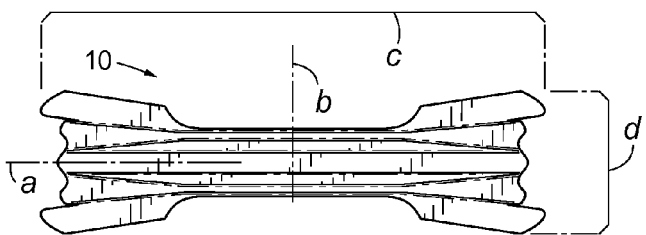
FIG. 4c
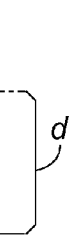

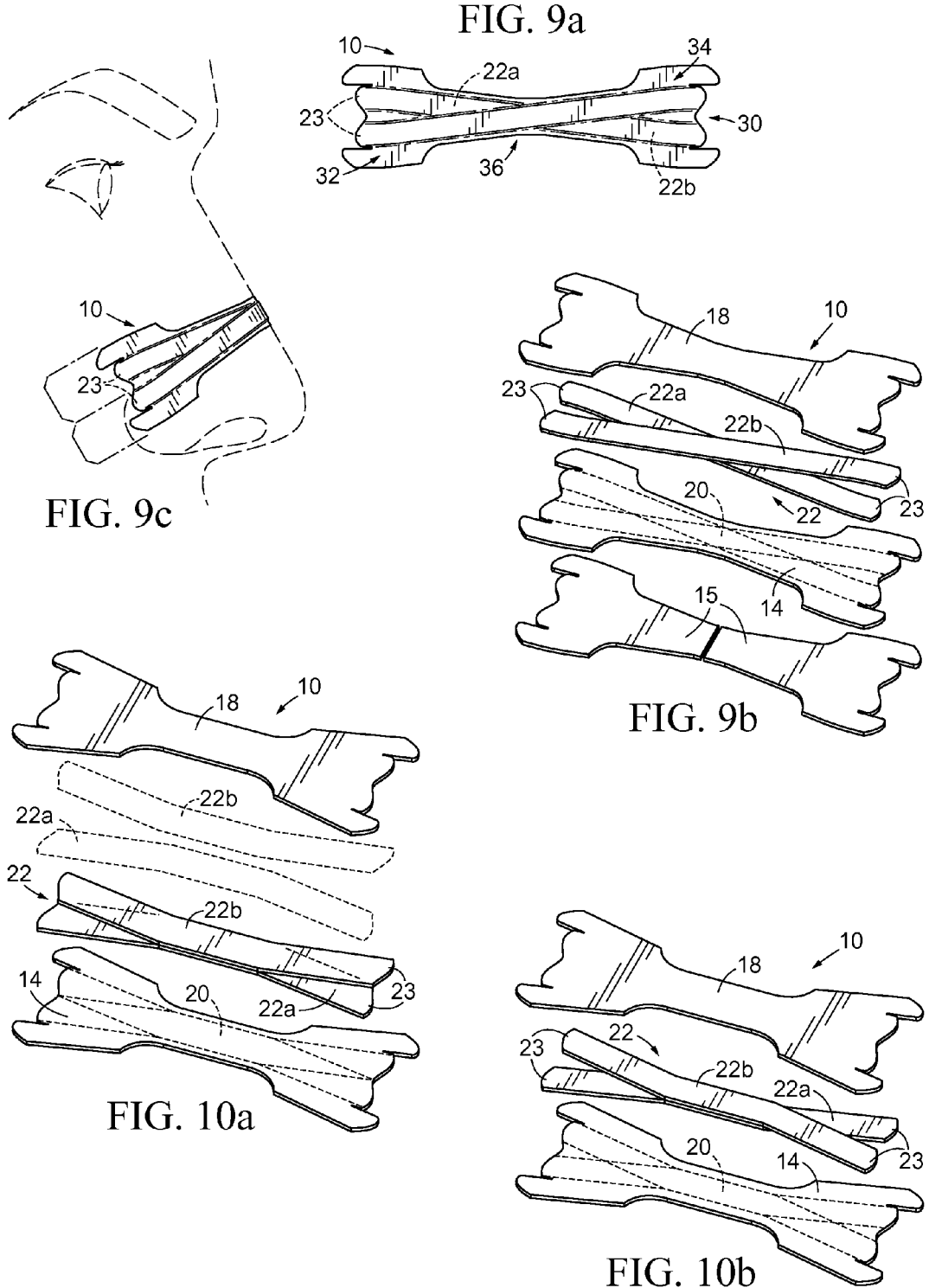

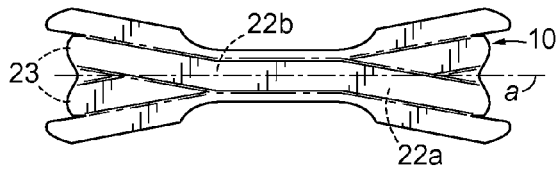
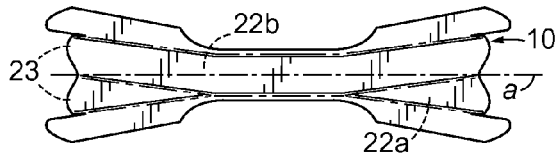
FIG. 10c
FIG. 11a
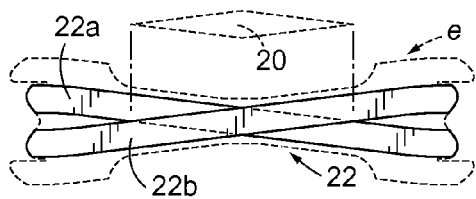
FIG. 11b
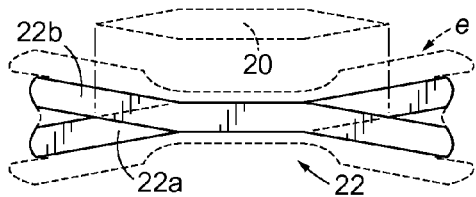
FIG. 11c
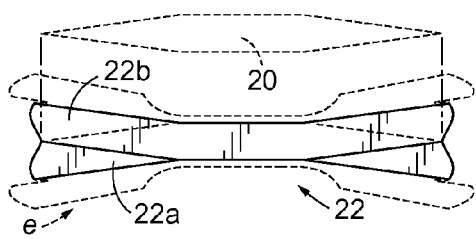
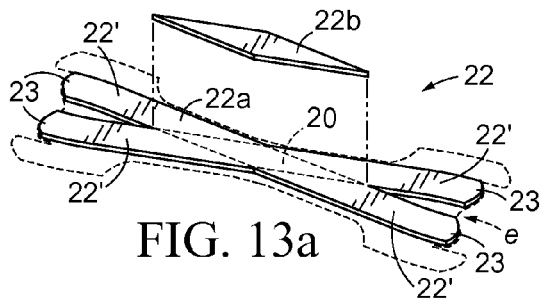
FIG. 13a
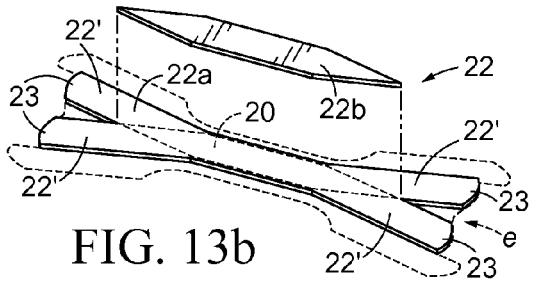
FIG. 13b
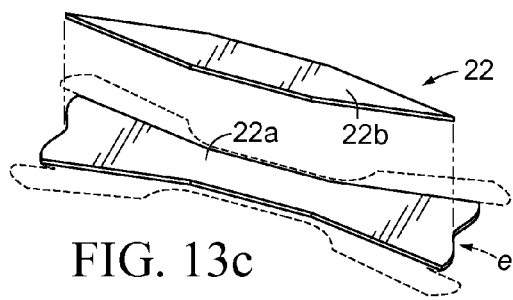
FIG. 13c

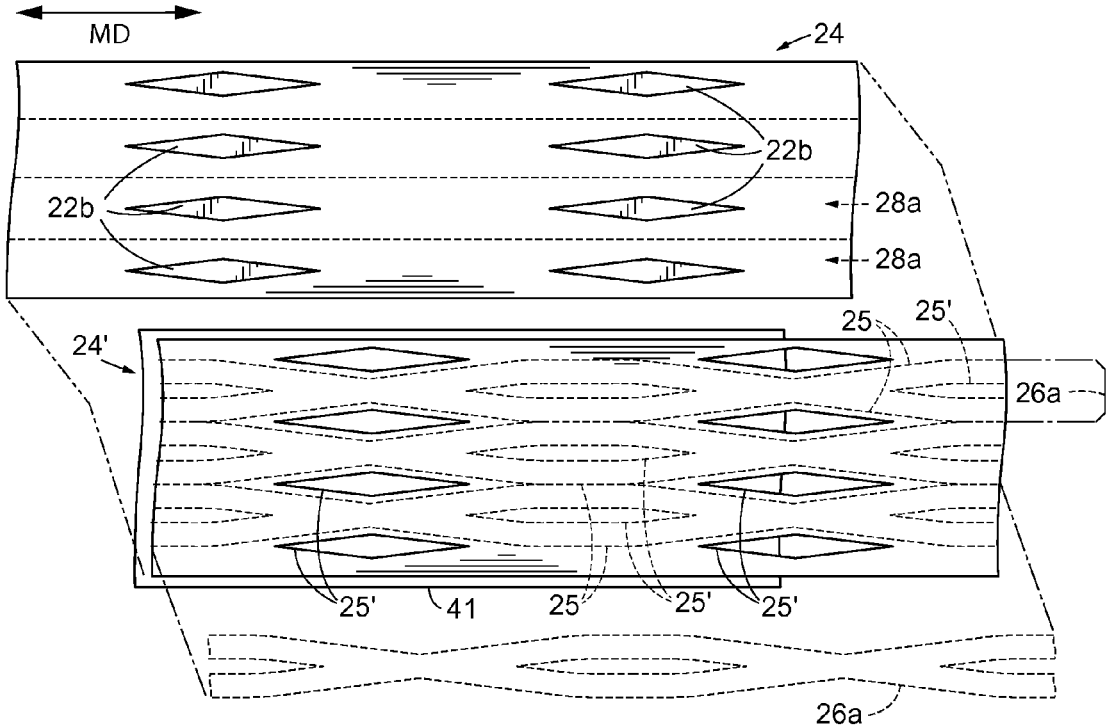
FIG. 14a
FIG. 14b
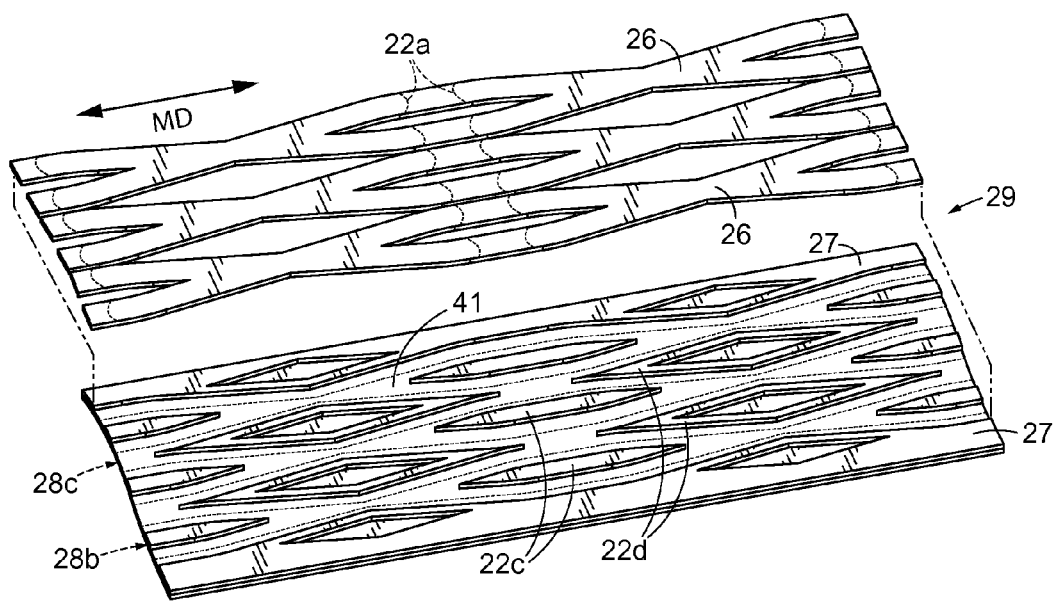

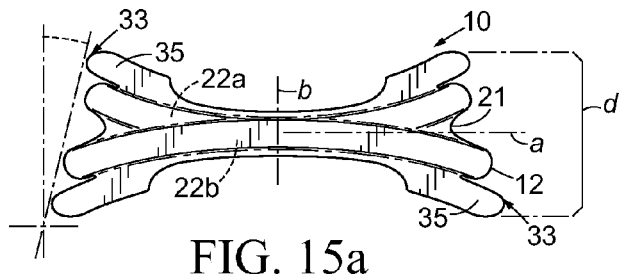
FIG. 15a
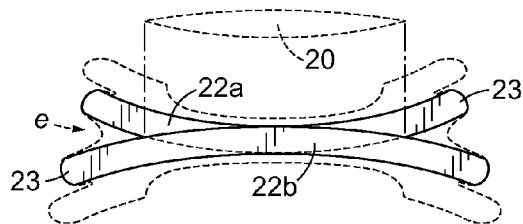
FIG. 15b
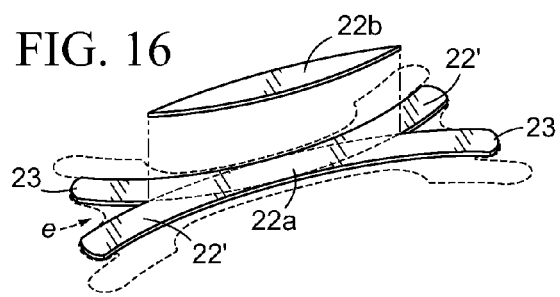
FIG. 16
FIG. 17a
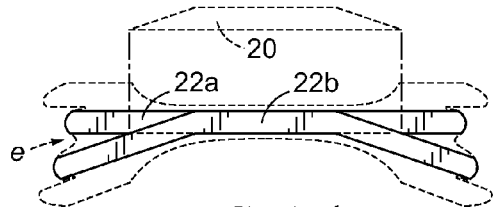
FIG. 17b
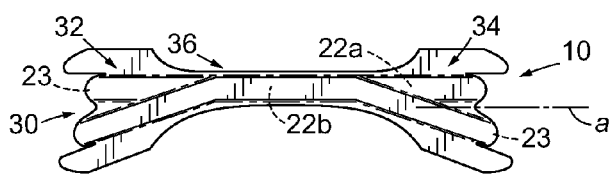
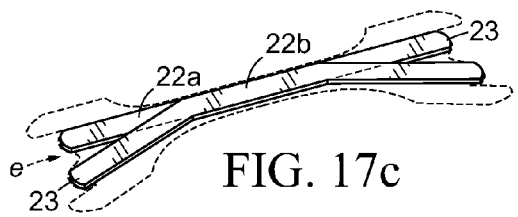
FIG. 17c
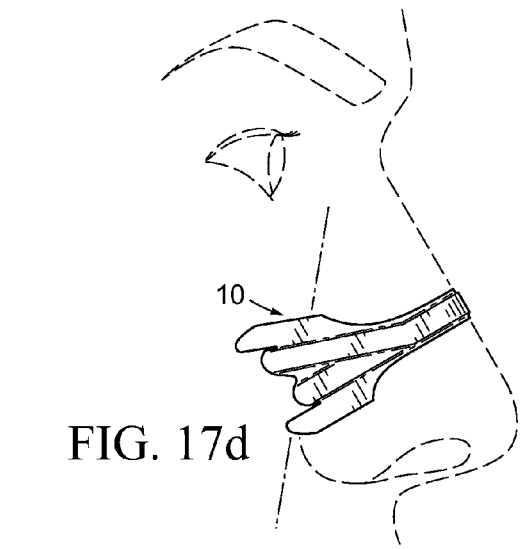
FIG. 17d
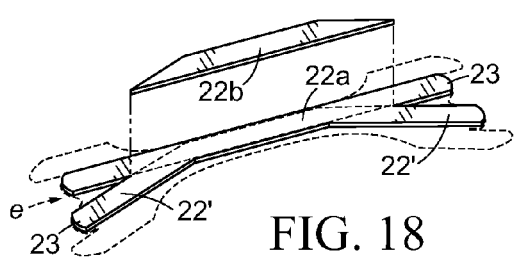
FIG. 18

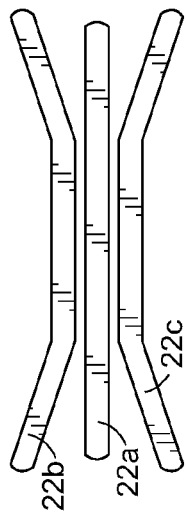
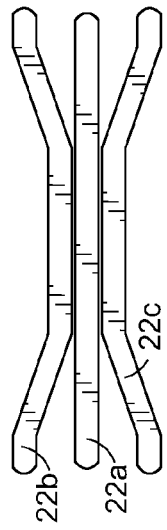
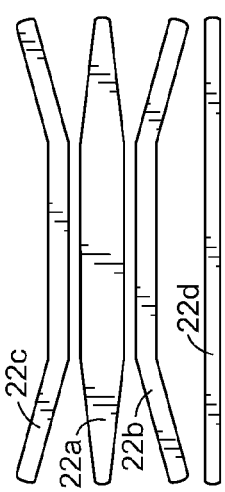
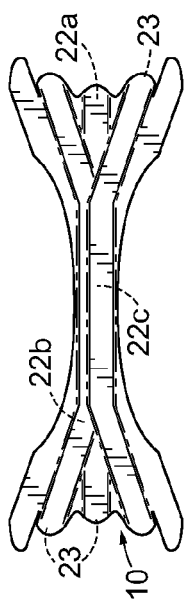
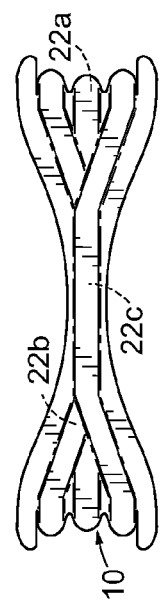
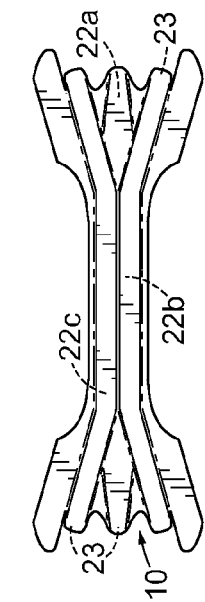
FIG. 20a  FIG. 21a  FIG. 22a
FIG. 20b  FIG. 21b  FIG. 22b

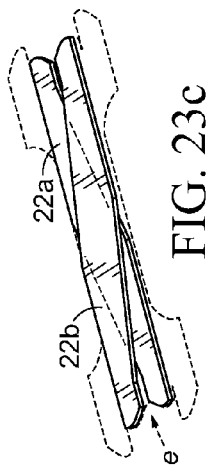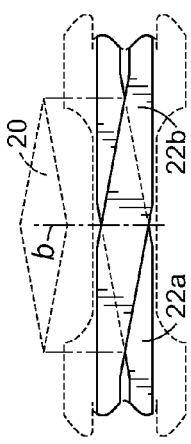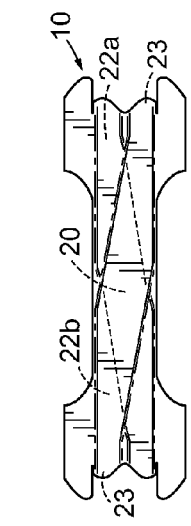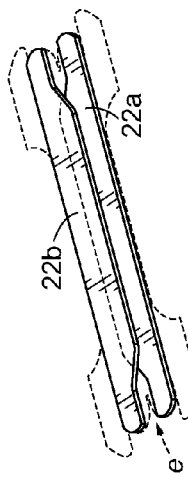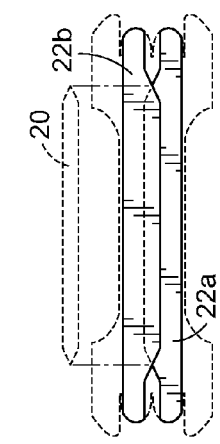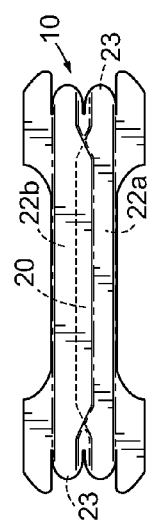

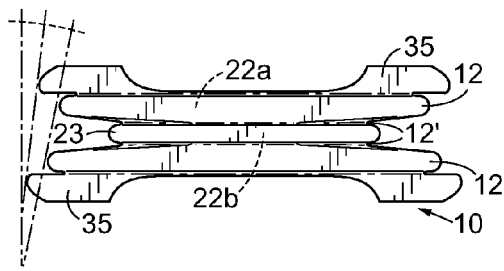
FIG. 28a
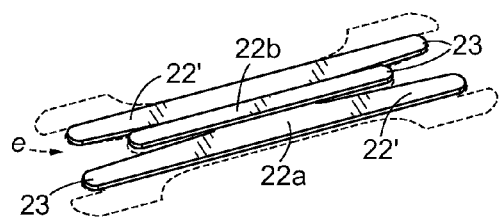
FIG. 28c
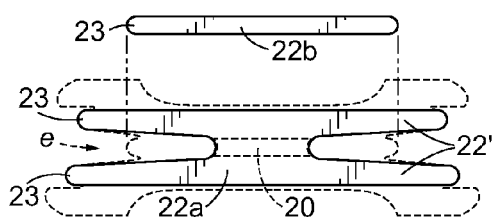
FIG. 28b
FIG. 29a
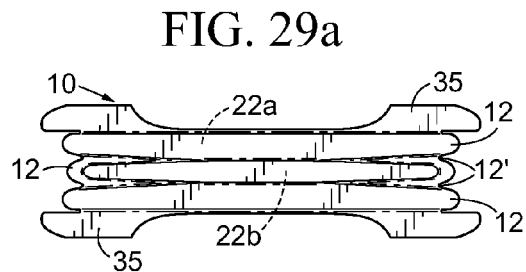
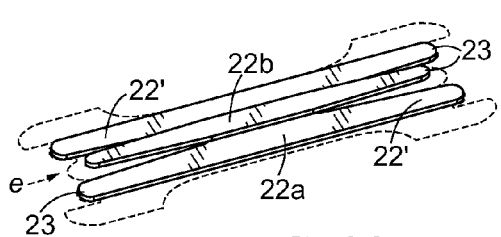
FIG. 29c
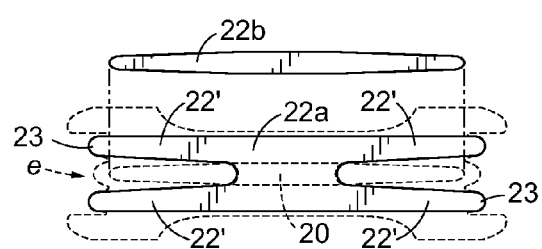
FIG. 29b

OVERLAPPING RESILIENT MEMBER STRUCTURES IN NASAL DILATOR DEVICES

RELATED APPLICATIONS

Not applicable.

FIELD OF THE INVENTION

The present invention relates generally to medical devices, and particularly to medical devices composed of at least two overlapping or overlaid components, including those medical devices having at least one component centrally registered, or island-placed, with at least one other component. The present invention further relates generally to methods of manufacturing, or converting, elongated sheets or rolls of thin flexible materials such as papers, thermoplastic films, foils, medical grade tapes, synthetic fabrics and the like into medical devices or components thereof.

The present invention relates more specifically to apparatus for and methods of dilating external tissue, and to methods of manufacturing tissue dilator devices for use in humans and equine athletes. As disclosed and taught in the preferred embodiments, the tissue dilator devices and methods of manufacturing tissue dilators or components thereof are particularly suitable for, and are directed primarily to, external nasal dilators used in supporting, stabilizing and dilating outer wall tissues of the nasal airway passages of the human nose. The United States Food and Drug Administration classifies the external nasal dilator as a Class I Medical Device.

BACKGROUND OF THE INVENTION

A segment of the human population has some malformation of the nasal passages that interferes with breathing, including deviated septa or inflammation due to infection or allergic reactions. Part of the interior nasal passage wall may draw in during inhalation to substantially block the flow of air. Blockage of the nasal passages as a result of malformation, or nasal congestion symptoms of the common cold or seasonal allergies are particularly uncomfortable at night, and can lead to sleep disturbances, irregularities and general discomfort.

In use the external nasal dilator is flexed across the bridge of the nose, extending over and engaging the nasal passage outer wall tissues on each side of the bridge, and held thereto by adhesive. A resilient member (synonymously referred to in the art as a spring, spring member, resilient band, resilient member band, or spring band) extends along the length of the device, embedded within or affixed thereto. When flexed across the bridge of the nose, the resilient member, having resiliency or resilient properties, exerts spring biasing forces extending from the middle of the dilator to its opposite end regions, which urges the nasal outer wall tissues outward, providing dilation and/or stabilization thereto. Stabilized or dilated tissue decreases airflow resistance within the nasal passages, allowing for a corresponding increase in nasal airflow. Increased nasal airflow may have a beneficial effect on nasal congestion, nasal snoring and obstructive sleep apnea.

A portion of the external nasal dilator art is suitable for mass production and commercialization in the consumer market, including devices disclosed in U.S. Pat. Nos. D379513, 6,453,901, D429332, D430295, D432652, D434146, D437641 and U.S. patent application Ser. Nos. 12/024,763, 12/106,289, 12/402,214, 12/964,746 and 29/380,763, the entire disclosures of which are incorporated by reference herein. Nasal dilators that have heretofore been widely available to consumers through a retail product category referred to generically as nasal strips include devices disclosed in U.S. Pat. Nos. D379513, 5,533,503, 5,546,929, RE35408, and 7,114,495.

The preferred thermoplastic material from which external nasal dilator resilient members are fabricated carries a significantly greater cost per unit of measure than other materials typically found in nasal dilator construction. Accordingly, simple resilient member structures, such as one or two rectangular resilient bands having a single thickness prevail in dilator devices that have been successfully commercialized. These resilient members are easily mass produced, extending the entire length of the dilator device so as to be severed at the dilator device ends in a continuous die-cutting process.

A single rectangular resilient member bisected lengthwise into two or three narrower, closely parallel members, each having the same thickness, length and width, is disclosed in the art. A single resilient member having divergent end portions, or multiple resilient member structures where one or more individual members have divergent end portions, are more recent in the art. In each case, the multiple resilient members are positioned adjacent each other and slightly spaced apart, as seen, for example, in U.S. Pat. No. 6,453,901 and U.S. patent application Ser. Nos. 12/024,763 and 12/106,289.

A dynamic relationship exists between dilator design and its efficacy, including resiliency, comfort and useful duration (i.e., the amount of time the device will remain effectively adhered to the skin). To be effective for a majority of users, a nasal dilator must generate from about 15 grams to about 35 grams of resiliency, or spring biasing force. Less than 15 grams may not provide enough stabilization or dilation, while greater than 35 grams would be uncomfortable for most users. The amount of spring biasing force is determined by the type of resilient member material used, its peripheral configuration, its overall width and length, and its thickness.

Nasal dilator resiliency creates primarily peel forces at the device end regions together with some tensile forces that work to disengage the device from the skin. External nasal dilators having design attributes that transform or redirect at least some disengaging peel and tensile forces into shear forces are disclosed in U.S. Pat. Nos. 5,533,503, 6,453,901 (FIGS. 10-11), and in U.S. patent application Ser. Nos. 12/106,289, 12/964,746 and 29/380,763. Shear forces are more easily withstood by adhesives typically used to engage nasal dilators to the skin surface of the nose. Other external nasal dilators, such as those disclosed in U.S. Pat. Nos. 6,543,901, 5,546,929 and RE35408 and U.S. patent application Ser. No. 12/402,214, overcome disengaging peel forces using an island-placed resilient member centrally registered within the device's peripheral edges. Skin-engaging material extends continuously outward beyond the peripheral edges of the resilient member, particularly from the opposite ends thereof, to overcome disengaging peel and tensile forces thereat. Island-placed resilient member structures are traditionally more costly to fabricate and have been less common in mass-produced dilator devices.

U.S. Pat. No. 6,375,667 (Ruch) discloses a nasal dilator having first and second resilient bands secured to first and second end regions of a flexible strip, plus a third resilient band interconnecting the first and second bands. The ends of the third resilient band overlap the inward ends of the first and second resilient bands, respectively, such that the three bands extend in a longitudinal line successively from end to end. U.S. Pat. No. 6,470,883 (Beaudry) discloses a nasal dilator having two stacked rectangular spring laminates (22, 24) that form a leaf spring (20). The upper laminate has a shorter length, but appears to have the same width and thickness as the lower laminate.

There is a continuing need in the art to address nasal dilator disengaging or delaminating peel forces, the dynamic relationship between adhesive engagement and spring biasing forces, and to economically manufacture on a mass scale nasal strip devices having complex resilient member structures of improved efficacy, durational longevity, and comfort. Furthermore, the nasal strip consumer product category has heretofore been dominated by a single brand, creating a pent up demand for innovation, competition, variety and complexity in nasal strip products.

SUMMARY OF THE INVENTION

Dilator devices of the present invention comprise a functional element, an engagement element, and a directional element in a laminate of vertically stacked layers formed as a unitary, single body truss. The truss comprises first and second end regions adapted to engage outer wall tissues of first and second nasal passages, respectively, and an intermediate region adapted to traverse a portion of a nose located between the first and second nasal passages. The truss is capable of resilient deformation; when flexed and released it returns to a substantially planar or pre-flexed state. In use the dilator stabilizes nasal outer wall tissues to prevent tissues thereof from drawing inward during breathing, and may further expand, or dilate, the nasal outer walls. The truss is configured to be comfortable on the skin surfaces engaged and to be easily removed with little or no stress thereto.

Embodiments of the present invention are directed to nasal dilators adapted for use on the human nose. With appropriate adjustments to size, resiliency, and engagement means, the dilator devices depicted herein may be adapted for use on equine athletes.

Dilator layers are formed in whole or part from elongated material webs combined with elongated material strands. Dilator layers are preferably secured to one another by an adhesive substance disposed on at least portions of at least one flat surface side of at least one layer. The resulting laminate of vertically stacked layers forms a unitary, or single body, truss. Each layer includes one or more members. A member may further include one or more components, as described herein. Each of the engagement, functional, and directional elements is defined by at least a portion of at least one layer of the dilator.

The functional element comprises a resilient member structure having resilient properties that generate spring biasing force or resiliency. (The terms spring biasing, spring biasing force, spring force, resiliency, spring constant, etc. as used herein are generally synonymous.) The engagement element affixes, adheres, or engages the dilator to the nasal outer wall tissues. The engagement element, by itself, does not provide nasal dilation, although depending on the material used and its specific construction, could provide tissue stabilization. A simple oblong resilient member configuration, as typically found in dilator devices, generally will not by itself remain adhered to the nasal outer wall tissues for a suitable length of time. Accordingly, dilator devices of the present invention preferably include an engagement element in the form of at least one dedicated dilator layer that defines at least a substantial portion of the body of the truss and its peripheral outline. Alternatively, resilient member structures of the present invention may form the truss in its entirety.

The directional element modifies, directs, affects or alters spring biasing properties generated by the functional element of the dilator so as to enhance device efficacy, engagement, useful duration, comfort or ease of use. The directional element includes one or more design features that: spread spring biasing forces to a greater lateral extent of the dilator; increase or decrease localized spring biasing forces; mitigate or transform delaminating peel and tensile forces, at least in part, from primarily peel forces to primarily shear forces; direct spring biasing forces to discrete contact points on each side of the bridge of the nose; create lessening of or gradiently reduce spring biasing forces at the device end regions.

Nasal dilator devices of the present invention include a resilient member structure comprising at least two resilient members, and often three or more resilient members, arranged in an overlapping or overlaid spatial relationship relative to each other. Where one resilient member overlays another, an overlap surface area may include the entirety of a flat surface of one member. Where resilient members overlap, an overlap surface area typically extends across the overlapping resilient members' mid-sections, corresponding to at least a portion of the intermediate region of the truss. Overlaid resilient members are typically parallel to each other. Overlapping resilient members may also be parallel to each other, or their long edges may intersect or cross at an oblique angle. Overlaid resilient members may have progressively less length or width: a lateral stepped reduction in width (and thus thickness) extending perpendicular from the longitudinal centerline of the truss, or a longitudinal stepped reduction in length (and thus thickness) extending parallel to the longitudinal centerline of the truss, or a combination of both.

Resilient member structures of the present invention also includes at least one non-overlap surface area, having a thickness, and at least one overlap surface area, having a thickness greater than any non-overlap surface area. Non-overlap surface areas are generally a first thickness. (An exception, for example, is if two overlapping resilient members are each a different thickness, and cross in the form of an X so as to form four non-overlap areas, two non-overlap areas will have a greater thickness and two non-overlap areas will have a lesser thickness.) Otherwise, one resilient member overlapping or overlaid onto another creates at least one overlap surface area having a second thickness equal to the combined thickness of the two members. A third overlapping/overlaid member creates at least one overlap area having a third thickness, and so on. The relationship between overlap and non-overlap surface areas is dynamic, determined by length, width, peripheral configuration, and the spatial relationship between the resilient members.

Resilient member structures of the present invention are configured to: create areas of greater and lesser thickness and thus corresponding resiliency; generate greater spring biasing forces along at least one overlap surface area compared to one or more non-overlap surface areas; gradiently reduce spring biasing forces across the width and/or along the length of the truss; form spring finger components of lesser thickness extending to discrete engagement contact points having lesser spring biasing force thereat; and create the effect of an additional island-placed resilient member without having to fabricate and position one. Embodiments of the present invention illustrate complementary overlapping and overlaid resilient member structures having similar dimensions and resilient properties; the former including at least one resilient member overlapping another, the latter including at least one resilient member overlaid and centrally registered with, or island-placed onto, another.

Individual resilient members of the present invention may be configured to any viable peripheral shape, size or thickness, and are configured to be fabricated in a continuous process. The continuous process forms resilient members end to end, spaced apart, or nested along common die cut lines so as to form complex structures with the same efficiency and economy as traditional or more simply constructed resilient members or structures. Continuous slits form elongated strands from one or more webs of resilient material; select strands are separated from the web and combined, or overlaid, with each other, then combined with at least one additional web and/or material strand to form a fabrication laminate from which finished dilator devices are die cut. The process may also form individual resilient members spaced apart and divided into strips that may be combined so as to island-place, or centrally register, the spaced apart members to each other. The process may also be applicable to those medical devices where overlapping or island-placed components are required.

The individual resilient members within a resilient member structure may be vertically separated by one or more of an intermediate material layer interposed therebetween so as to separate one or more resilient members into two or more resilient layers. The intermediate layer may comprise an adhesive substance or a flexible material, or both. The intermediate layer may further contribute to the engagement element of the dilator, particularly where the resilient member structure forms the body of the truss in its entirety, or intermediate layer may define at least a portion of the truss peripheral outline.

The present invention builds upon the prior art and discloses new, useful, and non-obvious resilient member structures comprising overlapped and overlaid resilient members, including methods of economically and efficiently mass producing said structures and incorporating them into dilator devices.

It is the principal objective of the present invention to provide novel nasal dilator devices having complex overlapping, overlaid and island-placed resilient member structures. A further objective of the present invention is to provide novel methods of fabricating said structures, and converting elongated flexible material webs into finished medical devices or components thereof, including means for centrally registering parts or components to each other.

The present invention is not limited to the illustrated or described embodiments as these are intended to assist the reader in understanding the subject matter of the invention. The preferred embodiments are examples of forms of the invention comprehended by that which is taught, enabled, described, illustrated and claimed herein. All structures and methods that embody similar functionality are intended to be covered hereby. The manufacturing methods depicted, taught, enabled and disclosed herein, while particularly suitable for dilator devices, may be applicable to other medical devices. The nasal dilators depicted, taught, enabled and disclosed herein represent families of new, useful and non-obvious devices having a variety of alternative embodiments. Dilator elements, layers, members, components, materials, or regions may be of differing size, area, thickness, length, width or shape than that illustrated or described while still remaining within the purview and scope of the present invention. The preferred embodiments include, without limitation, the following numbered discrete forms of the invention, as more fully described herein.

Some embodiments of the present invention are arranged in groups so as to illustrate similarly configured resilient member structures or to illustrate manufacturing steps. Each group introduces a new or subsequent feature, design element, manufacturing technique, or variation thereof. Accordingly, later embodiments may refer to, or cross reference, previous embodiments. It will be apparent to one of ordinary skill in the art that device or component configuration, techniques, methods, processes, etc., may be applied, interchanged or combined from one embodiment or group thereof to another. Elongated material webs are generally shown in the drawings as only wide enough to illustrate the subject at hand. In practice, said widths may be greater, and in some cases lesser. The longitudinal extents of material webs, where shown, are fragmentary.

For descriptive clarity, certain terms are used consistently in the specification and claims: Vertical refers to a direction parallel to thickness, such as the thickness of a finished device, a material web, material layers, or a material laminate. Horizontal refers to length or longitudinal extent, such as that of a finished device, or a direction parallel thereto. Lateral refers to width, such as that of a finished device or a material web, and to a direction parallel to the cross direction (XD) of a material web. Longitudinal refers to length, such as that of a finished device, or the length or machine direction (MD) of a material web, or a direction perpendicular to width or lateral extent. A longitudinal centerline is consistent with the long axis of a finished device or material web, bisecting its width midway between the long edges. A lateral centerline bisects the long edges of a finished device or material web midway along its length, and is perpendicular to the longitudinal centerline. An object or objects referred to as adjacent or consecutive another generally means laterally, consistent with the width of a finished device or a material web. Objects referred to as successive are generally oriented lengthwise, end to end, parallel to the machine direction (MD) of a material web. The terms upper and lower may be used, particularly in plan views, to refer to object orientation on a drawing sheet.

Broken lines and dashed lines are used in the drawings to aid in describing relationships or circumstances with regard to objects:

- A broken line including a dash followed by three short spaces with two short dashes therebetween indicates separation for illustrative purposes, such as in an exploded view, or to indicate an object or objects removed or separated from one or more other objects as the result of a process or method.
- A dashed line of successive short dashes with short spaces therebetween may be used to illustrate an object, such as one underneath another; or for clarity, to show location, such as the space an object or structure will occupy, would occupy, or did occupy; or for illustrative purposes, to represent an object, structure or layer(s) as 'invisible' so that other objects more pertinent to the discussion at hand may be highlighted or more clearly seen.
- A broken line including a long dash followed by a short space, a short dash and another short space is used to call out a centerline or an angle, or to indicate alignment; when accompanied by a bracket, to call out a section, segment or portion of an object or a group of objects; to illustrate a spatial relationship between one or more objects or groups of objects, or to create separation between objects for the purpose of illustrative clarity.

In the drawings accompanying this disclosure, like objects are generally referred to with common reference numerals or characters, except where variations of otherwise like objects must be distinguished from one another. Where there is a plurality of like objects in a single drawing figure corresponding to the same reference numeral or character, only a portion of said like objects may be identified. After initial description in the text, some reference characters may be placed in a subsequent drawing(s) in anticipation of a need to call repeated attention to the referenced object. In describing manufacturing methods, Machine Direction is indicated in the drawings by the letters 'MD' adjacent a directional arrow: a single arrowhead indicates preferred direction; a double arrowhead indicates flow may be in either direction. Drawings are not rendered to scale, and where shown, the thickness of objects is generally exaggerated for illustrative clarity.

BRIEF DESCRIPTION OF THE SEVERAL VIEWS OF THE DRAWING

FIG. 1b is an exploded perspective view of the nasal dilator of FIG. 1a.

FIG. 2b shows two sectional views comprising two and three resilient members, respectively, on an enlarged scale, taken along the lines 2-2 in FIG. 2a.

FIG. 2c is a sectional view of the resilient member structure of FIG. 2b comprising three resilient members and further including intermediate material layers.

FIG. 3 is a cross sectional view of adjacent parallel resilient members shown for comparison to FIG. 2b.

FIG. 4a is an exploded perspective view of a second form of nasal dilator in accordance with the present invention.

FIG. 4b is a fragmentary plan view on an enlarged scale of the end region of the second form of nasal dilator in accordance with the present invention.

FIG. 4c is a plan view of the nasal dilator of FIG. 4a.

FIG. 5 is a plan view of the individual resilient members comprising the resilient member structure of the nasal dilator of FIG. 4.

FIG. 7b is a plan view of the individual resilient members comprising the resilient member structure of the nasal dilator of FIG. 7a.

FIG. 7c is an exploded perspective view of the nasal dilator of FIG. 7a.

FIG. 9a is a plan view of a fourth form of nasal dilator in accordance with the present invention.

FIG. 9b is an exploded perspective view of the nasal dilator of FIG. 9a.

FIG. 9c is a side elevation showing the attachment of the nasal dilator of FIG. 9a to the nose of a wearer depicted in broken lines.

FIGS. 10a and 10b are exploded perspective views illustrating an alternative configuration of the fourth form of nasal dilator.

FIG. 10c is a plan view of the nasal dilators shown in FIGS. 10a and 10b.

FIGS. 11a-11c are plan views highlighting the resilient member structures of the nasal dilators shown in FIGS. 9 and 10.

FIGS. 13a-13c are exploded perspective views highlighting the resilient member structures of a fifth form of nasal dilator in accordance with the present invention.

FIG. 14a is a plan view illustrating the initial steps of a fourth form of manufacturing method in accordance with the present invention by which to fabricate member structures substantially as seen in FIG. 13.

FIGS. 14b-14d are exploded perspective views illustrating subsequent steps of the third manufacturing method.

FIGS. 15a and 15b are plan views of a sixth form of nasal dilator in accordance with the present invention.

FIG. 16 is an exploded perspective view highlighting the resilient member structure of a seventh form of nasal dilator in accordance with the present invention.

FIGS. 17a and 17b are plan views of a eighth form of nasal dilator in accordance with the present invention.

FIG. 17c is a plan view highlighting the individual resilient members comprising the resilient member structure illustrated in FIG. 17b.

FIG. 17d is a side elevation showing the attachment of the nasal dilator of FIG. 17a to the nose of a wearer depicted in broken lines.

FIG. 18 is a perspective view highlighting the resilient member structure of a ninth form of nasal dilator in accordance with the present invention.

FIGS. 20a, 21a, and 22a are plan views of three variations of a tenth form of nasal dilator in accordance with the present invention.

FIGS. 20b, 21b and 22b are plan views of the individual resilient members comprising the resilient member structures illustrated in FIGS. 20a, 21a, and 22a, respectively.

FIGS. 23a, 24a, and 25a are plan views of three variations of an eleventh form of nasal dilator in accordance with the present invention.

FIGS. 23b, 24b, and 25b are plan views highlighting the resilient member structures of the nasal dilators illustrated in FIGS. 23a, 24a, and 25a, respectively.

FIGS. 23c, 24c and 25c are perspective views highlighting the resilient member structures of the nasal dilators illustrated in FIGS. 23a, 24a, and 25a, respectively.

FIGS. 28a, and 29a are plan views of two variations of a fourteenth form of nasal dilator in accordance with the present invention.

FIGS. 28b and 29b are plan views highlighting the resilient member structures of the nasal dilators illustrated in FIGS. 28a and 29a, respectively.

FIGS. 28c and 29c are perspective views highlighting the resilient member structures of the nasal dilators illustrated in FIGS. 28a and 29a, respectively.

FIG. 30b is an exploded perspective view highlighting the resilient member structure of the nasal dilator of FIG. 30a.

FIG. 31b is a perspective view highlighting the resilient member structure of the nasal dilator of FIG. 31a.

FIG. 33b is an exploded perspective view highlighting the resilient member structure of the nasal dilator of FIG. 33a.

FIG. 34b is a perspective view highlighting the resilient member structure of the nasal dilator of FIG. 34a.

DETAILED DESCRIPTION OF THE INVENTION

Figure 1A:
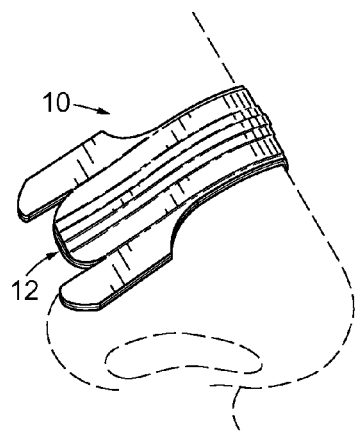
FIG. 1a is a perspective view showing a human nose, depicted in broken lines, with the attachment thereon of a first form of nasal dilator in accordance with the present invention.

An embodiment of a nasal dilator, 10, in accordance with the present invention is illustrated in FIG. 1. Shown in use, dilator 10 is engaged to a human nose, represented by dashed lines. FIG. 1a illustrates a horizontal protrusion, 12, which separates slightly from the skin thereat as a result of the dilator end region structure, a directional element that shifts a portion of spring biasing forces from primarily peel forces to primarily shear forces, so as to improve engagement to the nasal outer wall tissues.

Figure 1C:
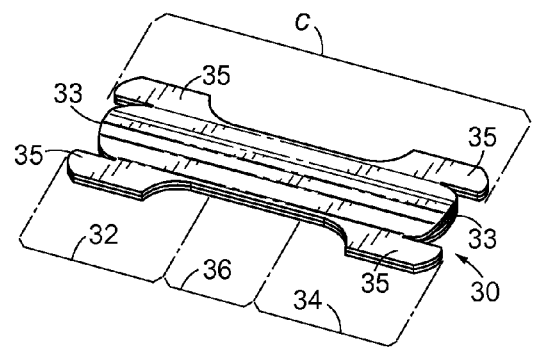
FIG. 1c is a perspective view of the nasal dilator of FIG. 1b.
Figure 1B:
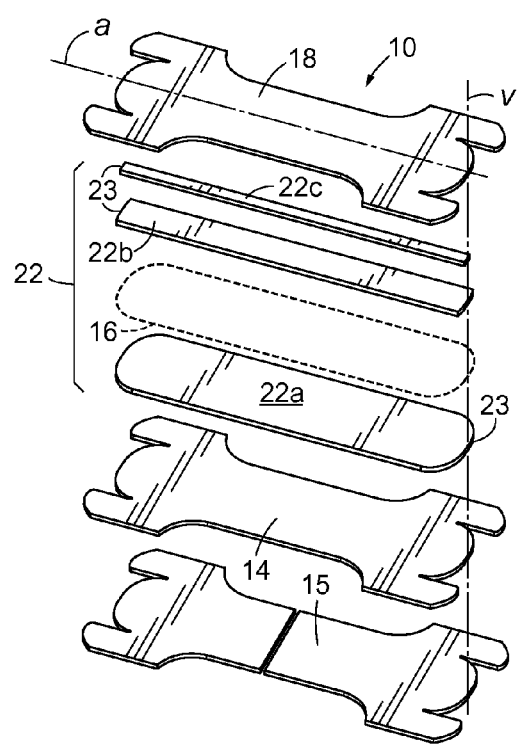

As seen more clearly in FIGS. 1b and 4a, dilator 10 comprises a laminate of vertically stacked layers aligned along a vertical centerline, v, and a longitudinal centerline, a, indicated by broken lines. Dilator layers include: a base layer comprising at least one base member, 14; a resilient member structure, 22, comprising at least one layer and a plurality of resilient members, 22a, 22b, and 22c; a cover layer comprising at least one cover member, 18; and one or more of an optional intermediate layer, 16, illustrated by dashed lines, which may be positioned between any two of the aforementioned layers or members. Any layer may overlap or overlay any other layer in whole or in part. The peripheral dimensions of dilator 10 may be defined, in whole or part, by resilient member structure 22, or by any dilator layer or portion thereof, or by any combination of layers.

A protective layer of release paper, 15, removably covers exposed adhesive from any other layer preliminary to using the dilator. The shape and dimensions of release paper 15 may correspond to the periphery of dilator 10 or may exceed the periphery of one or more dilators 10. Release paper 15 may be bisected into two parts, which may overlap or abut, so as to facilitate removal from the dilator prior to use.

The base and cover layers of dilator 10 may be fabricated concurrently so as to have the same peripheral shape. Alternatively, the base and resilient layers may be fabricated concurrently to the same peripheral shape or the base layer may have a greater surface than the resilient layer(s) but lesser than the cover layer. The base and cover layers may be interchanged, the base and/or cover layers may be eliminated in whole or in part, or the cover layer may be interposed between the resilient layer and the skin surfaces engaged by the dilator. The cover layer may be divided into two parts, one each substantially defining each end region of the dilator.

Where the base layer has a significantly lesser surface area than the cover layer, adhesive on the skin-engaging side of the base layer may be optionally eliminated in whole or part. With or without adhesive, the base layer may also serve as a compressible buffer between the device and the skin, as has been historically common in medical devices that remain in contact with the skin for any length of time.

Dilators of the present invention generally include dedicated functional and engagement elements: the resilient member structure providing the former and the base layer and/or cover layer, and optionally the intermediate layer, providing the latter. Alternatively, resilient member structures of the present invention are configured, or otherwise may be configured, to form the truss in its entirety. Specifically, structures having a directional element that significantly reduces and/or laterally spreads spring biasing forces across the lateral extent of the truss, particularly at the end regions thereof, and resilient member structures comprising multiple engagement contact points are generally suitable or adaptable for use without the addition of a separate, dedicated engagement element. Of necessity, however, these structures preferably include an adhesive substance disposed on at least a portion of the tissue-engaging surface(s) thereof.

Dilator layers may be secured to each other by any suitable means such as stitching or fastening, heat or pressure bonding, ultrasonic welding, or the like, but are preferably laminated by an adhesive substance disposed on at least one flat surface side of at least one layer. This may be in addition to or in lieu of intermediate layer 16, which may comprise an adhesive substance, a carrier material, or a carrier material with an adhesive substance disposed on one or both flat surface sides whereby to bond two dilator layers together.

The preferred material for the dilator base and cover layers is from a group of widely available flexible nonwoven synthetic fabrics that are breathable and comfortable on the skin. Any suitable fabric or thermoplastic film, or various clear films, including high Moisture Vapor Transmission Rate (MVTR) polyurethane film, are suitable. A pressure sensitive adhesive, preferably biocompatible with external human tissue, may be disposed on at least one flat surface side of the material. A protective, removable, release liner covers the adhesive. The preferred materials are typically available in rolls wound in the machine direction (MD), or warp, of the material, which is perpendicular to the cross direction (XD), or fill, thereof.

The preferred material for the dilator resilient members is a widely available biaxially oriented polyester resin (PET), a thermoplastic film having suitable spring biasing properties across both its warp and fill. The material may have a pressure sensitive adhesive disposed on one or both flat surfaces covered by a removable protective release liner. PET may be laminated to the preferred base layer material, from the adhesive side of the former to the non-adhesive side of the latter, so that at least one resilient member and the base layer of dilator 10 may be die cut concurrently.

The functional element of dilator 10 is configured to provide spring biasing force within a suitable, or functional, range as described hereinbefore. The functional element of the present invention comprises a plurality of resilient members positioned, at least in part, in an overlapping or overlaid relationship in one or more resilient layers. Spring biasing force and its directional application is determined by the dimensional configuration of each resilient member and the combined resilient members, or resilient member structure, including overlap and non-overlap surface areas. A resilient member may have an adhesive substance disposed on at least a portion of at least one of two opposite flat surface sides for engaging or laminating it to other layers, members or components of dilator 10, or for adhering directly to the nasal outer wall tissues.

FIG. 1c illustrates that the layers of dilator 10 form a unitary, or single body, truss, 30, having a length, or longitudinal extent, c, indicated by broken lines and a bracket. Truss 30 has contiguous regions indicated generally by broken lines and brackets, including a first end region, 32, a second end region, 34, and an intermediate region, 36, which joins first end region 32 to second end region 34.

The truss end regions provide the primary surface area engagement to the nasal outer wall tissues on each side of the bridge of the nose. The width of intermediate region 36 is preferably narrower than the width of end regions 32 and 34. Portions of any layer may define a region of the truss or a portion thereof. The layers, members or components of dilator 10 may extend from one region to another. In the preferred embodiments end regions 32 and 34 are shown as identical in peripheral configuration and in size and shape. That is, they are the mirror images of each other. However, it will be apparent to one of ordinary skill in the art that they may be configured asymmetric or non-identical in size, shape or scale.

Figure 2A:
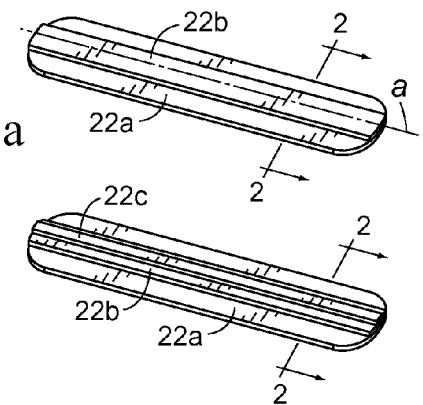
FIG. 2a shows two perspective views of resilient member structures seen in FIG. 1 comprising two and three resilient members, respectively.

FIGS. 1 and 2 illustrate an overlaid resilient member structure of the present invention in its simplest form. A flat surface side of at least one resilient member is overlaid onto at least a portion of a flat surface side of at least one other resilient member. The resilient members are substantially parallel to each other, and include a first resilient member, 22a, a second resilient member, 22b, and a third resilient member, 22c. A resilient member has opposite terminal ends, 23, which may extend to, align with, or conform to a portion of each end edge of dilator 10, or extend short of either end edge. The resilient members may be stacked in any order, but are preferably stacked from wider to narrower. One or more resilient members may be optionally positioned as the uppermost, or visible, layer when the dilator is seen in a top-down plan view or engaged to the nose. The resilient members are generally of similar shape, but may be of different size, thickness, width or length.

Figure 2B:
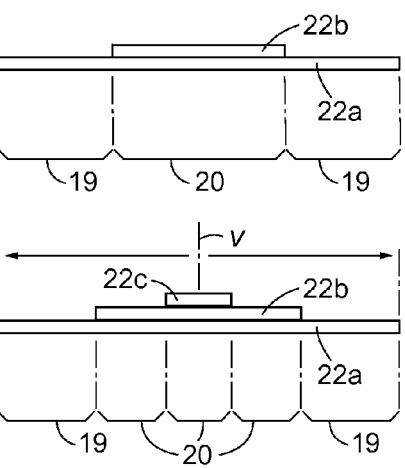

FIG. 2b shows overlaid resilient members 22a and 22b forming an overlap surface area, 20, as well as non-overlap surface areas, 19, as indicated by broken lines and brackets. Resilient member 22c in turn overlays resilient member 22b, which creates another overlap surface area. (Note: whether resilient members overlay or overlap, the area of resulting combined thickness is always referred to by the term "overlap area" or "overlap surface area".) The resilient layer structure thus has at least one non-overlap surface area having a first thickness; overlaid resilient member 22b creates at least one overlap surface area of a second thickness, and overlaid resilient member 22c creates at least one overlap surface area of a third thickness. Directional arrows illustrate a stepped reduction from greater to lesser thickness of the resilient member structure, and thus a corresponding stepped reduction in resiliency thereof, extending laterally from longitudinal centerline a and vertical centerline v to respective outer long edges of resilient member 22a. The number of steps corresponds to the number of overlaid resilient members.

The thickness of respective overlap surface areas 20 shown in FIG. 2b is equal to the combined thickness of the overlaid resilient members. The same stepped reduction in thickness may be seen in multiple parallel resilient member bands of varied thickness, spaced apart slightly, as shown for comparison by cross section in FIG. 3: the outermost bands have a thickness corresponding to non-overlap areas; the band(s) inboard thereof have greater thickness corresponding to overlap surface areas. The adjacent resilient members seen in FIG. 3 would have slightly greater axial, torsional flexibility in a dilator device than the fewer resilient members overlaid as seen in FIG. 2. However, the resilient member structure of FIG. 2 may have a lower manufacturing cost.

FIG. 2c shows that resilient members may be vertically separated by intermediate layer 16 interposed therebetween, dividing the resilient member structure into two or more resilient layers. Intermediate layer 16 preferably comprises a very thin, inexpensive flexible material, such as a synthetic fabric or thermoplastic film, having an adhesive substance disposed on at least one flat surface side. Alternatively, intermediate layer 16 may comprises an unsupported transfer adhesive. Depending on the material type, intermediate layer 16 may be used as a matter of structural integrity, manufacturing efficiency or expediency (see FIG. 19), or to aid alignment of dilator layers. It may also be used as the engagement element of the dilator, in whole or part. The periphery or width and length of intermediate layer 16 may be lesser or greater than the individual resilient members, or other dilator layers, separated thereby.

As noted, the overlaid resilient member structure shown in FIGS. 1 and 2 is a simple form thereof, having substantially rectangular members with straight, substantially parallel, long edges. FIG. 4 illustrates a second form of nasal dilator in accordance with the present invention: an overlaid resilient member structure that directs spring biasing forces to a wider area at the end regions of the truss. As in FIGS. 1 and 2, a flat surface side of resilient member 22b is overlaid onto 22a, and a flat surface side of resilient member 22c is overlaid onto resilient member 22b. However, resilient member 22a is wider at its ends and resilient member 22b is narrower at its ends, as particularly illustrated by broken lines and bracket in FIG. 5.

The spring biasing of a single resilient member in a dilator device is generally no greater than that determined by the width and thickness at the resilient member mid-section. (Absent material separations, such as relief cuts, openings, notches, etc., formed in the resilient member, greater width and/or thickness at its mid-section generally means greater spring biasing force, and narrower width and/or lesser thickness at the resilient members ends generally lessens that spring biasing force.) The wider end portions of resilient member 22a thus do not necessarily increase spring biasing force, but do spread the resilient member spring constant across a greater lateral extent at the ends. Overlaid by resilient members 22b and 22c, however, the resiliency of the resilient member structure, as a whole, is increased. That increase occurs primarily along longitudinal centerline a, with the greatest spring biasing force generated at where the long edges of the overlaid resilient members are parallel to each other.

That increased resiliency is manipulated, or directed, at least in part, at end regions 32 and 34 of the truss; spread laterally by the increased width of resilient member 22a, and simultaneously decreased, at least in part, by the tapered portions of resilient member 22b. It will be apparent to one of ordinary skill in the art that the dimensions of the tapered portions of resilient members 22b and 22a are dynamic, and may be adjusted or configured relative to each other, along with the overall dimensions of all resilient members, in order to achieve a desired spring biasing constant and/or direction of spring biasing properties.

As seen in FIG. 4b, each truss end region has elements associated with an end edge, 33, including: at least one tab extension, 35, at least one horizontal protrusion 12, a material separation of various forms, including a notch, 13, and a valley, 12'. Protrusion 12 generally corresponds to terminal end 23 of a resilient member, or as is the case in FIG. 4b, corresponds to a portion of a' resilient member end edge. Valley 12' is generally interposed between two protrusions 12. Notch 13 is interposed between tab extension 35 and an adjacent protrusion 12. A material separation may also comprise a slit, back cut, indentation, slot, elongated opening, or other form, extending inward or outward from a peripheral edge (typically end edge 33) of the dilator, or from the end edge of a resilient member or other dilator layer.

End region elements may help the dilator conform to the contours of nasal outer wall tissues, and as a directional element, may direct spring biasing properties by changing the angle of focused spring biasing forces, at least in part, thus shifting or transforming at least some of these forces from primarily peel and tensile forces into primarily shear forces. The change in angle further redistributes or imparts said transformed forces to tissue engaging surface areas of the end regions, such as tab extensions 35, extending beyond the material separation. Spring biasing forces are thus imparted to the lateral width and longitudinal extent of end regions 32 and 34, as opposed to a greater delaminating tendency from peel forces being imparted to a lesser extent. Shear forces are more easily withstood by the tissue engaging adhesives disposed on the engagement element of dilator 10 than are peel forces.

FIG. 4c indicates the width, or lateral extent, d, of dilator 10 by broken lines and a bracket. Lateral centerline, b, is also indicated by a broken line, and generally aligned to the bridge of the nose. Dilator 10 is symmetric on each side of lateral centerline b, each horizontal half of dilator 10 being identical, one side being the mirror image of the other. Dilator 10 is also laterally symmetric on each side of its longitudinal centerline a. However, dilator 10 may be laterally asymmetric; end edge 33 and its associated elements may be angled inward from one long edge of the dilator to the opposite long edge, for example, making the upper long half of the dilator shorter than the lower long half so as to better correspond to the somewhat triangular shape of the nose.

FIG. 6 illustrates a method by which dilator resilient members 22a and 22b, substantially as illustrated in FIG. 4, may be concurrently fabricated. FIG. 6a shows a plurality of a continuous slit, 25, spaced across the width of elongated web of resilient material, 24. Resilient material 24 preferably has a layer of adhesive disposed on one side covered by a removable protective release liner. Continuous slits 25 extend vertically through material web 24 and generally parallel to the machine direction thereof. Slits 25 form a plurality of elongated resilient material strands, 26a and 26b. Each outside edge of web 24 may include an outside waste strand, 27, the purpose of which is to allow for minor lateral drift of the material web or webs as they pass through the die cutting machinery.

Figure 6A:
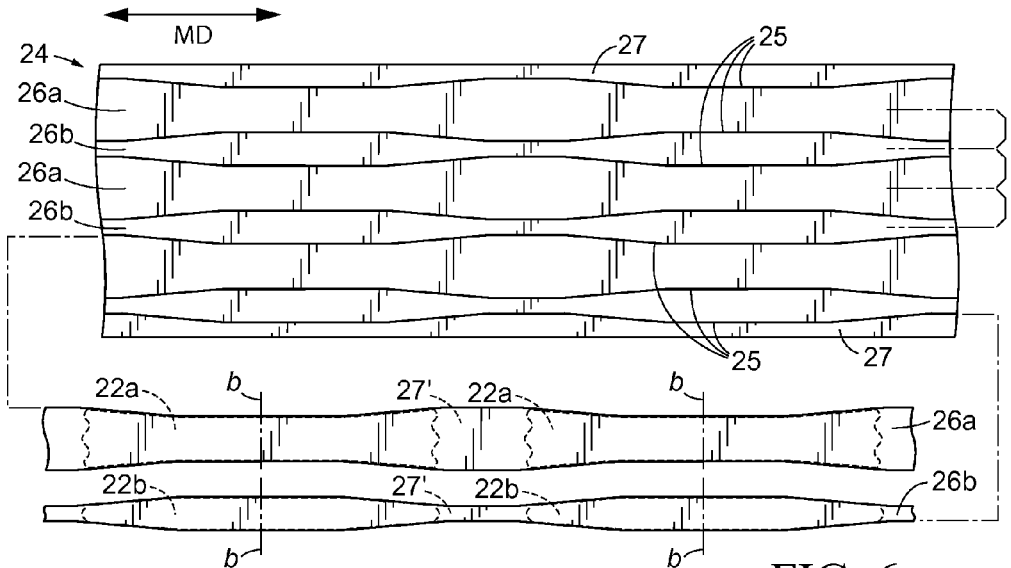
FIGS. 6a and 6d are plan views illustrating initial steps of a first form of manufacturing method in accordance with the present invention by which to fabricate individual resilient members comprising resilient member structures substantially as illustrated in FIG. 4.

FIG. 6a further illustrates that portions of the long edges of resilient material strands 26a and 26b correspond to the long edges of a plurality of resilient members 22a and 22b, respectively, interconnected end to end by waste pieces, 27'. Since strands 26 consist of a plurality of interconnected resilient members, then each continuous slit 25 forms, as well as defines, at least a portion of one long edge of the interconnected resilient members adjacent to each side of the slit, the long edges of adjacent interconnected resilient members thus being on common lines.

Figure 6B:
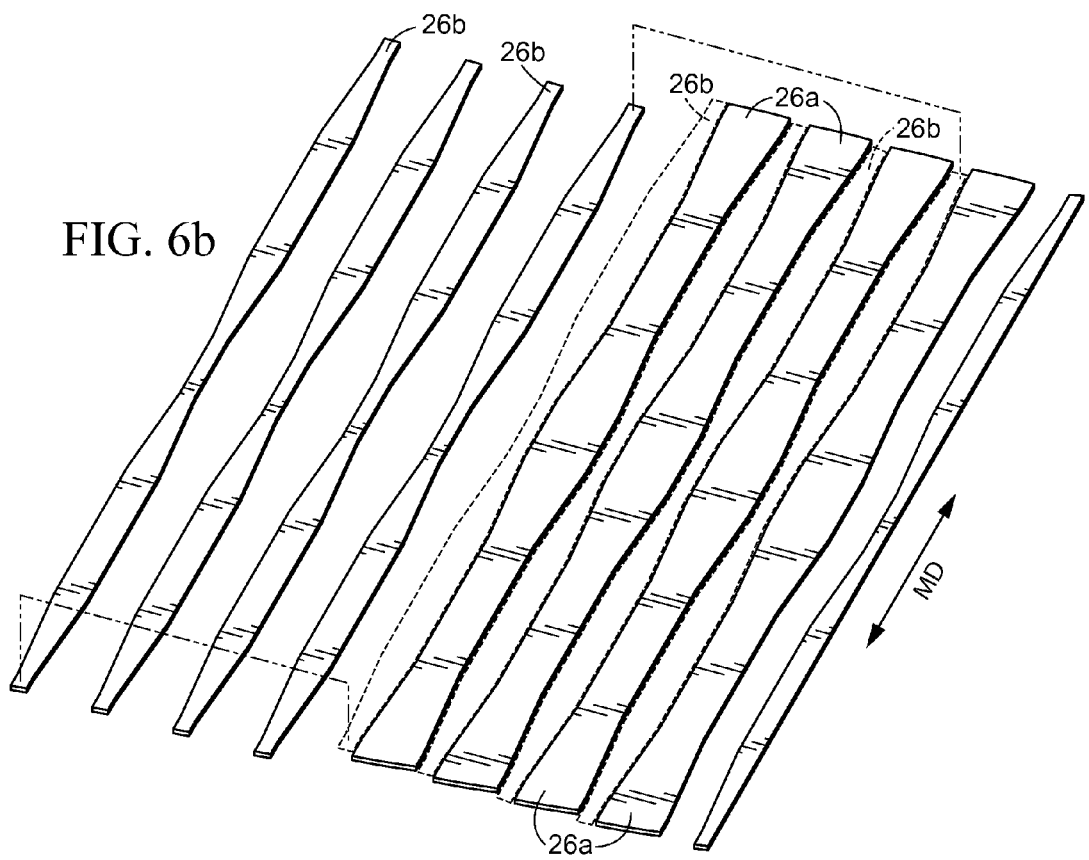
FIGS. 6b, 6c and 6e perspective views illustrating subsequent steps of the first manufacturing method.
Figure 6C:
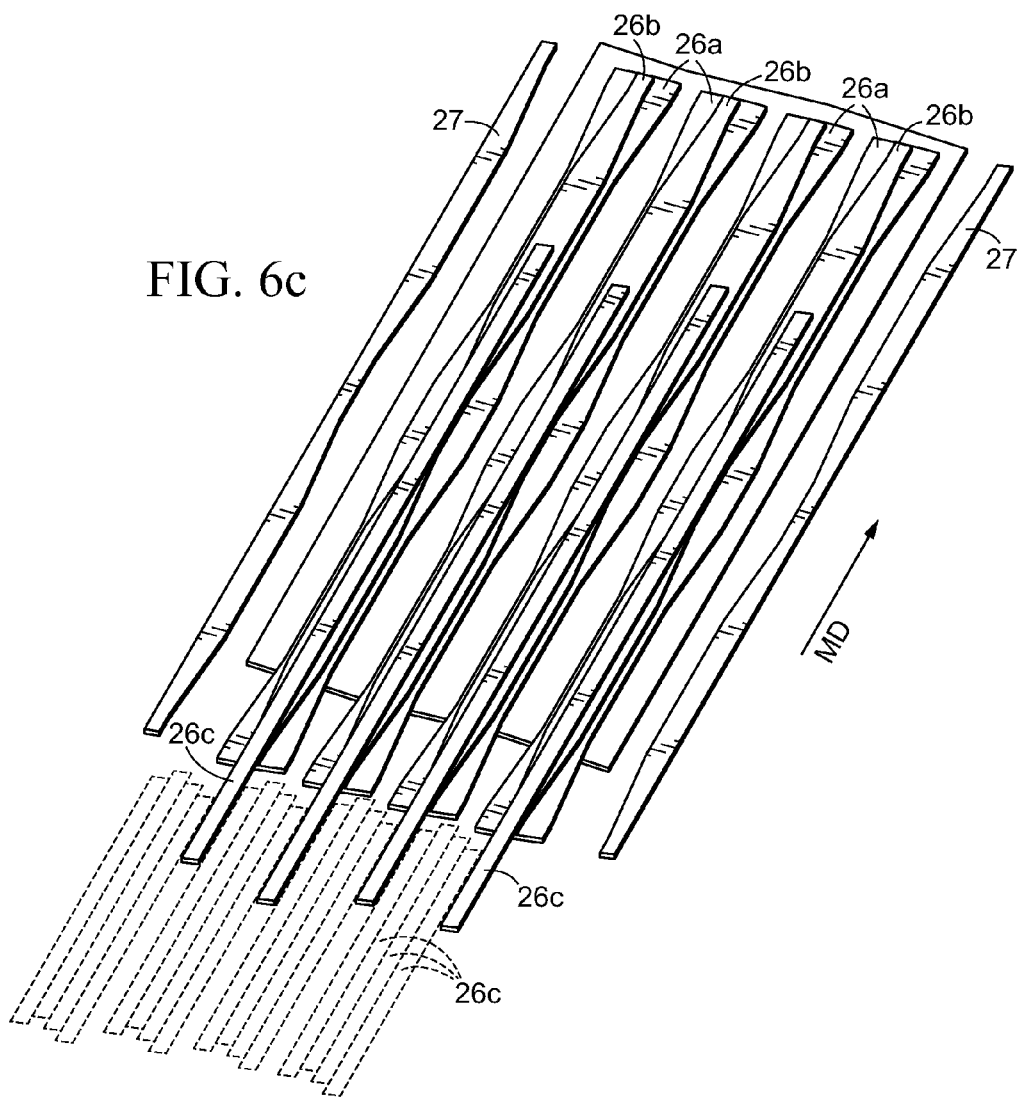

By virtue that resilient material strands 26a and 26b alternate laterally, side by side, their longitudinal centerlines are spaced equidistant, as indicated by broken lines and brackets. The strands are thus pre-registered to each other so that when separated into respective groups, as seen in FIG. 6b, one group may be positioned squarely onto the other group, as seen in FIG. 6c, without having to align each individual strand. Dashed lines illustrate the respective ends of interconnected resilient members 22a and 22b, which are laterally adjacent, thus their lateral centerlines b are aligned, as indicated by broken lines. Accordingly, the interconnected resilient members are pre-registered to each other, both laterally and longitudinally, before the separated groups of resilient material strands are overlaid.

Figure 6D:
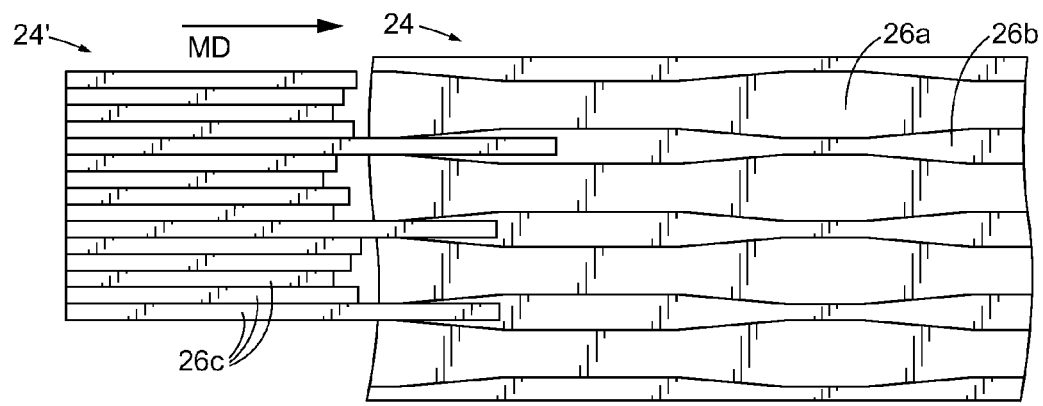

In FIG. 6b, dashed lines illustrate the spaces in between resilient material strands 26a formerly occupied by strands 26b. FIG. 6c shows strands 26a, as a group, positioned onto a corresponding group of strands 26b. Elongated resilient material strands 26c, which correspond to continuous interconnected resilient members 22c, may be formed from a separate elongated web of resilient material, 24', seen in FIG. 6d. FIGS. 6c and 6d further illustrate that one strand 26c out of a plurality thereof (each 1 in 5, as shown) aligns with and is overlaid onto each of combined strands 26a and 26b. It will be apparent to the skilled practitioner that resilient material webs 24 and 24' may be of different thickness, and so also the respective elongated strands produced therefrom.

Figure 6E:
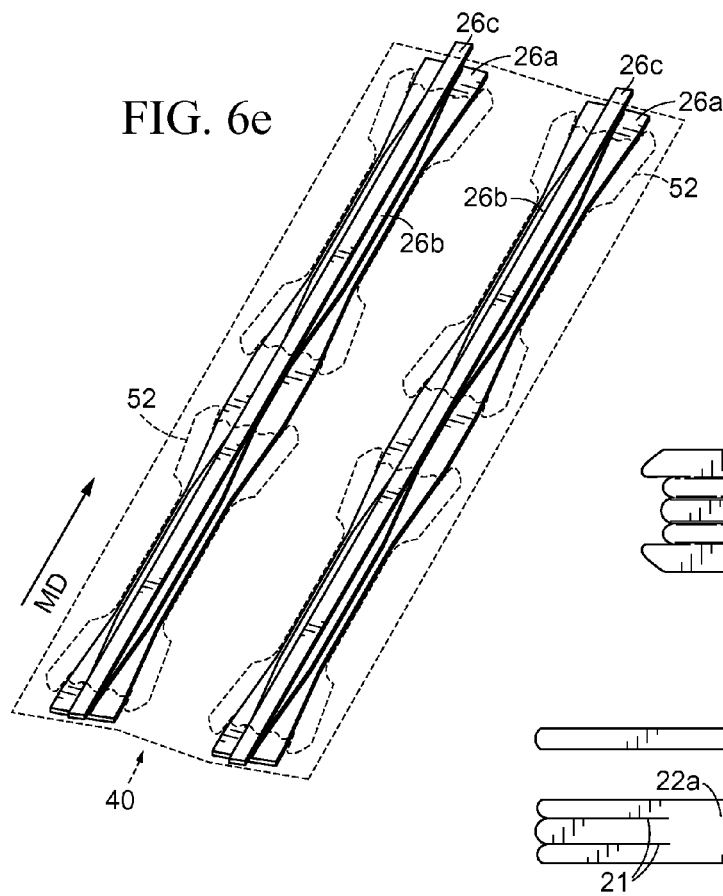

FIG. 6e illustrates combined overlaid resilient material strands 26a, 26b and 26c laminated with at least one additional material web corresponding to at least one additional layer of dilator 10 so as to form a fabrication laminate, 40. Laminate 40 may include at least one of a base layer material web or cover layer material web and a protective release liner. Prescribed die cut lines, 52, corresponding to the peripheral outline of finished dilator devices, extend vertically through fabrication laminate 40 to form finished dilators. In the process, die cut lines 52 sever strands 26 at the opposite end edges of each finished dilator device to form overlaid resilient member structure 22.

FIG. 7 illustrates a third form of nasal dilator in accordance with the present invention wherein a narrower, substantially rectangular, resilient member 22b is overlaid onto a portion of the width of a wider resilient member 22a. Resilient member 22a includes at least three pairs of spring finger components, 22', extending longitudinally outward from a common center to terminal ends 23. This resilient member structure approximates that of three adjacent parallel, substantially rectangular resilient member bands, and wherein at least one band has a greater thickness. In the present instance, that greater thickness is provided by overlaid resilient member 22b, which extends substantially parallel to resilient member 22a.

Spring fingers components 22' are defined, at least in part, by material separations in the form of a slit, 21, extending inward from the end edges of resilient member 22a. Spring fingers 22' could alternatively be separated by a slot or elongated opening, which would then define lateral spacing, or distance, between the spring finger inside long edges. Spring fingers 22' may be of any length or width so as to influence or direct resilient properties independently to each long half of the resilient member. However, they are preferably substantially uniform. Depending upon the length of slits 21, resilient member 22a may have greater axial, torsional flexibility along its length, particularly near its ends. Greater flexibility generally allows dilator 10 to more closely conform to surface irregularities of the nasal outer wall tissues.

Figure 7A:
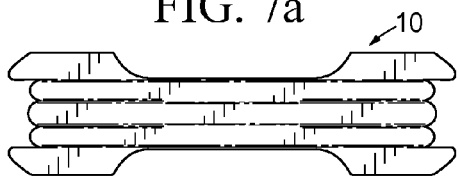
FIG. 7a is a plan view of a third form of nasal dilator in accordance with the present invention.
Figure 7B:
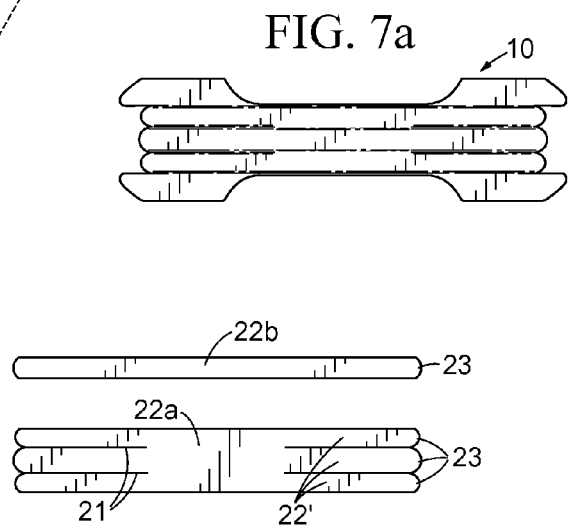
Figure 7C:
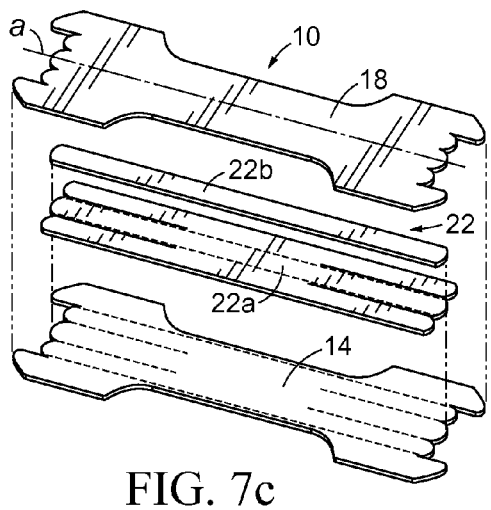
Figure 7D:
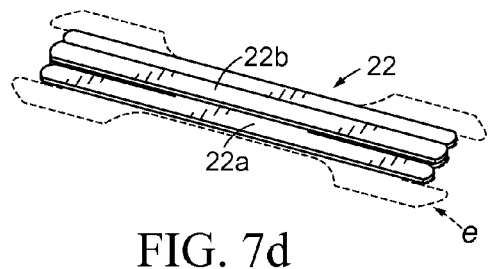
FIG. 7d is a perspective view highlighting the resilient member structure shown in FIG. 7c.

Resilient member 22b is preferably longitudinally aligned to at least one spring finger 22', its width preferably no greater than the width of the spring finger overlaid, so as to add its thickness thereto and increase resiliency along thereat. FIG. 7d more particularly illustrates resilient member 22b being slightly narrower than the width of the pair of opposing spring finger components 22' onto which it is overlaid. As shown, resilient member structure 22 is configured so that dilator 10 generates greater spring biasing force along centerline a. Alternatively, resilient member 22b may be longitudinally aligned to at least one slit 21 so as to divide its width across two or more spring finger components.

FIG. 7d also shows the engagement element, e, of dilator 10 represented by dashed lines in the form of the dilator periphery. Engagement element e may comprise any layer, or portion thereof, or any combination of layers that make up the engagement element, as described hereinbefore. The dilator engagement element is occasionally referenced in this manner in some embodiments of the present invention to particularly illustrate features and construction of the dilator functional element in the form of resilient member structure 22 and the constituent resilient members thereof. The reference symbol e may alternatively indicate that the dilator engagement element may be optional; the resilient member structure thus forming the truss substantially in its entirety, as described hereinbefore.

Figure 8:
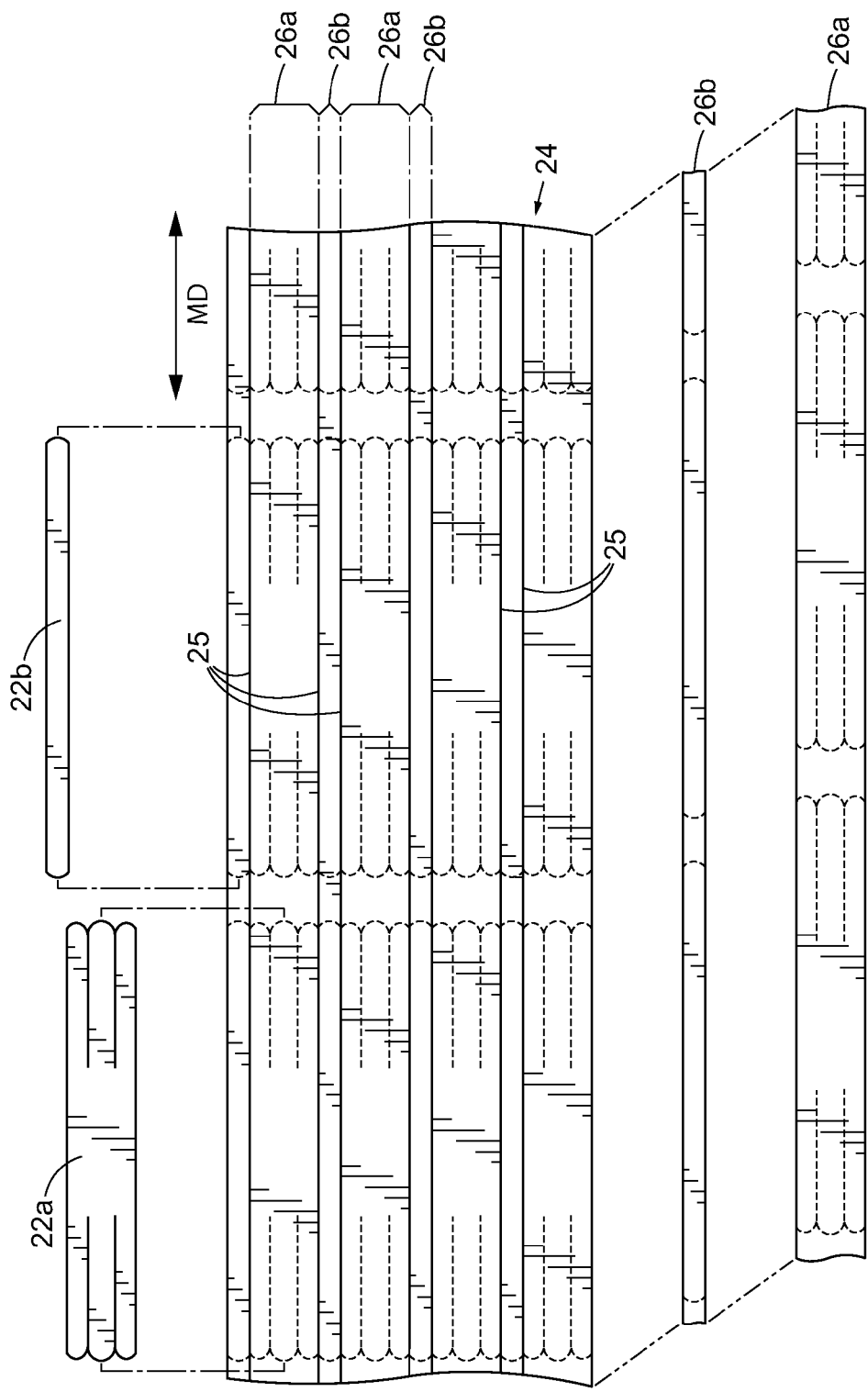
FIG. 8 is a plan view of a second form of manufacturing method by which to fabricate the individual resilient members comprising the resilient member structure of the nasal dilator of FIG. 7.

FIG. 8 illustrates that dilator resilient members 22a and 22b, particularly as seen in FIG. 7, may be concurrently fabricated along common die cut lines substantially as described previously with respect to FIG. 6. A plurality of continuous slit 25 spaced across a web of resilient material 24 forms alternating resilient material strands 26a and 26b, as indicated by broken lines and brackets. The long edges of the strands correspond to the long edges of a plurality of successive interconnected resilient members 22a and 22b, as indicated by broken lines and dashed lines.

By virtue that resilient material strands 26a and 26b alternate side by side, their longitudinal centerlines are spaced equidistant. When separated into respective groups, one group may be overlaid squarely onto the other without having to align individual strands. The aligned overlaid strands may be combined with at least one additional material web corresponding to at least one additional layer of dilator 10 so as to form a fabrication laminate from which finished dilator devices are die cut.

FIGS. 9 and 10 illustrate a fourth form of nasal dilator in accordance with the present invention, wherein a portion of a flat surface side of at least one resilient member overlaps a portion of a flat surface side of at least one other resilient member. At least one long edge of one resilient member intersects a long edge of another resilient member. FIG. 9 shows that resilient members 22a and 22b overlap by crossing at their respective mid-sections. Each resilient members has the same width and parallel long edges; the shape of overlap surface area 20 is thus a parallelogram or rhombus. Substantially rectangular resilient members may cross in the form of an X, as shown in FIG. 9, or alternatively, resilient members having a rectangular mid-section and divergent end portions may overlap along said mid-sections and cross, as shown in FIG. 10b, or not cross, as shown in FIG. 10a.

The width of the resilient members, the angle at which they cross, or the angle at which said end portions diverge, is dynamic, and may be configured to direct resilient properties in a predetermined manner. Furthermore, the size and peripheral dimensions of overlap surface area 20 are influenced by the respective widths of the resilient members (a narrower width forms a lesser overlap surface area; a greater width forms a greater portion), by the angle at which the resilient members cross (a greater crossing angle forms a lesser overlap surface area; a narrower angle forms a greater portion), or by the degree of angle at which opposite ends of the resilient member diverge from the mid-section. It will be apparent to one of ordinary skill in the art that resilient members of a different shape or width would change the shape or size of overlap surface area 20 accordingly.

The longitudinal extent and peripheral shape of overlap surface areas 20 as seen in FIGS. 9 and 10 are particularly illustrated in FIG. 11: FIG. 11a corresponds to the dilator illustrated in FIG. 9; FIG. 11b corresponds to FIG. 10b, and FIG. 11c corresponds to FIG. 10a. FIG. 11 shows that as overlap surface area 20 extends progressively more toward the opposite end edges of dilator 10 there is correspondingly less lateral separation between respective resilient member terminal ends 23 at the opposite end edges of the truss, to the point where there is no lateral separation at all, as in FIG. 11c.

As seen in FIGS. 9 and 10, overlapping resilient member structures include non-overlap surface areas comprising spring finger components extending outward from a common center of greater thickness, the common center defined by overlap surface area 20. The spring biasing force generated by the resilient member structure is thus spread laterally and outward to four discrete engagement contact points that correspond to respective resilient member terminal ends 23 (which also corresponds to truss end edge element protrusion 12). As indicated by broken lines and brackets in FIG. 9c, the upper contact points may be positioned on the nose adjacent the nasal valve, the lower contact points over the nostril area or nasal vestibule.

FIG. 10a illustrates that resilient members 22a and 22b may overlap without crossing. The resilient members are identical, but flipped laterally from each other. Instead of crossing, the resilient members overlap along their mid-sections, with the two divergent end portions of each resilient member being on the same side of longitudinal centerline a. Overlap surface area 20 has parallel long edges and the shape of a hexagon or six-sided polygon. By comparison, the end portions of the resilient members in FIG. 10b diverge to each side of the long edges of the overlaid mid-sections. The dilators of FIGS. 10a and 10b are further illustrated in the plan view in FIG. 10c.

In overlapping resilient member structures, one resilient member may have greater resiliency than the other, such as by greater thickness or width. As seen in FIGS. 9a and 9c, for example, if resilient member 22a is thicker than resilient member 22b, outer wall tissues above the nasal valve would be subject to greater spring biasing, while tissues around the nostril would have lesser spring biasing. The reverse would be true at the opposite end region of the truss on the other side of the bridge of the nose. If the resilient members overlap, but do not cross, as shown in FIG. 10a, spring biasing at respective resilient member terminal ends would be the same at each end region of the truss, and thus the same on each side of the bridge of the nose.

Resilient member structures like those illustrated FIGS. 9-11 may be fabricated substantially as discussed previously with respect to FIG. 6, with the difference, as seen in FIG. 12, that elongated resilient material strands 26a and 26b are configured so as to overlap, or cross, in a continuous pattern. The strands are preferably identical, and are labeled "26a" and "26b" for descriptive clarity.

Elongated resilient material strands 26a and 26b are slit from respective resilient material webs 24 and 24', which are aligned to at least one additional material web corresponding to fabrication laminate 40. All webs are shown fragmentary. FIG. 12 illustrates that each strand 26a and 26b include repeating portions that extend parallel to the long edges of fabrication laminate 40, and portions that diverge obliquely therefrom. For illustrative clarity, resilient material webs 24' and 24 are depicted as being on opposite sides of laminate 40. In practice, the webs would be positioned relative to each other and to laminate 40 so that a group of select strands 26a and 26b, from x plurality thereof (as shown, each 1 of 6 or each 1 of 7) may be peeled from the respective webs and incorporated into laminate 40 such that the repeating portions of the strands cross in a continuous pattern.

The lengths of resilient material webs 24 and 24' and the at least one additional material web corresponding to laminate 40 are preferably very similar. Webs 24 and 24' must be shifted slightly to re-align with laminate 40 as each group of 1 from x number of resilient material strands 26 and 26a are peeled away. Once the desired resilient layer strands 26 and 26a are overlapped and incorporated into laminate 40, prescribed die cut lines 52, corresponding to the peripheral outline of finished dilator devices, extend vertically through fabrication laminate 40 to form finished dilators. In the process, die cut lines 52 sever strands 26 at the opposite end edges of each dilator device to form overlapping resilient member structure 22. Laminate 40 may include at least one of a base layer material web or a cover layer material web, and a removable protective release liner, as described hereinbefore.

Figure 12A:
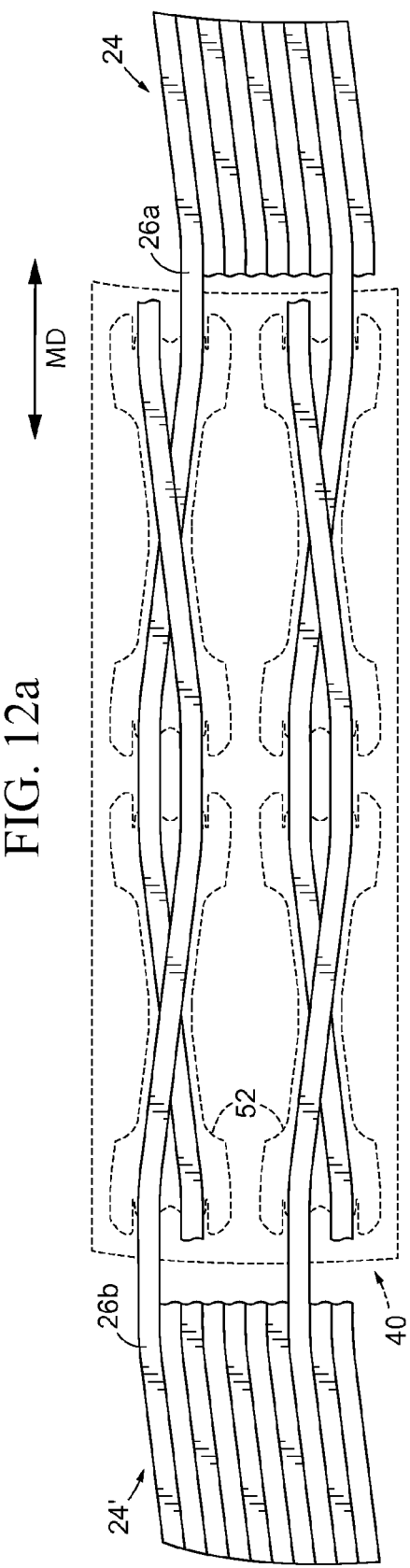
FIGS. 12a and 12b are plan views of a third form of manufacturing method in accordance with the present invention by which to fabricate resilient member structures substantially as illustrated in FIGS. 9 and 10.
Figure 12B:
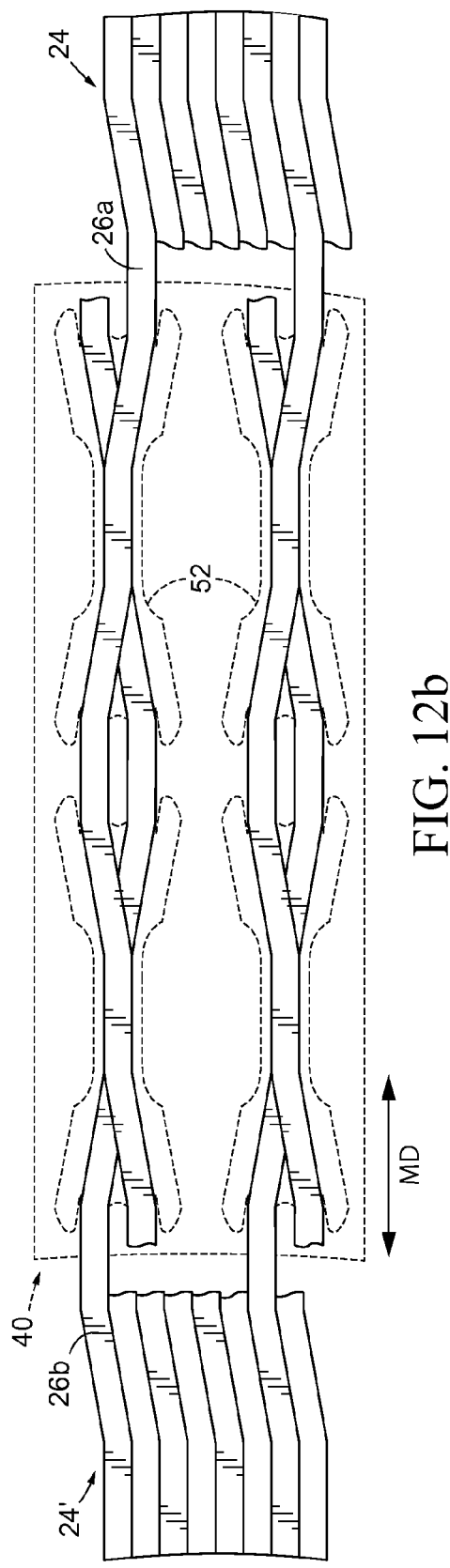

FIG. 12a applies particularly to the resilient member structure seen in FIG. 9. As such, the overlaid portions of resilient material strands 26a and 26b correspond to the aforementioned portions that diverge obliquely. FIG. 12b illustrates the resilient member structure seen in FIG. 11b as an example, in which case the overlaid portions of the strands correspond to those portions that are parallel to the long edges of the web. In either case, FIG. 12 illustrates that the continuous crossing pattern forms a plurality of an overlapping resilient member structure in which the non-overlap surface areas comprise spring finger components extending outward from a common center; the common center in turn defined by the overlap portion, as described previously. This type of overlapping resilient member structure is also discussed with regard to FIGS. 15, 17, 20-22, and 23-25, all of which may be fabricated by the method of FIG. 12.

FIG. 13 illustrates a fifth form of nasal dilator in accordance with the present invention, depicting overlaid resilient member structures similar to the overlapping resilient member structures of FIG. 11. In particular, FIG. 13a corresponds to FIG. 11a; FIG. 13b to FIG. 11b, and FIG. 13c to FIG. 11c. The overall configuration of overlap and non-overlap surface areas, and the resilient properties of the respective resilient member structures of one embodiment are effectively, or alternatively, re-created in the other.

Each resilient member 22a seen in FIG. 13 has a peripheral outline at least similar, if not identical, to the periphery of the combined overlapped resilient members 22a and 22b of FIG. 11. Accordingly, resilient member 22a, as seen in FIGS. 13a and 13b, is formed to include spring finger components 22' extending outward from a common center to discrete engagement contact points at each end region of the truss. Resilient member 22a may also be viewed as including a material separation in the form of a roughly triangular shaped opening extending inward from each end edge. The opening defines the inside long edges of the spring finger components and the lateral separation between upper and lower discrete contact points. While the configuration of resilient member 22a is shown similar to the peripheral outline of the resilient member structure shown in FIG. 11, spring finger components 22' may alternatively be any shape or configuration: straight, curved, or having a constant or tapered width.

FIG. 13 further illustrates resilient member 22b, having the respective rhombus or hexagon shape of overlap surface area 20 seen in FIG. 11, overlaid and centrally registered with, or island-placed onto, resilient member 22a, extending between the opposing points at which spring finger components 22' diverge. (Note that the structure of FIG. 13c is generally similar to that of FIG. 4, discussed previously.) Respective resilient member thickness being equal, the resilient member structures of FIGS. 9-11 and FIG. 13 will have similar spring biasing properties. Both structures and their corresponding engagement elements may be efficiently converted into dilator devices using methods substantially as described herein.

As previously discussed with regard to FIG. 7, the spring biasing of a single resilient member in a dilator device corresponds to the narrowest width at its mid-section. Resilient member 22a seen in FIG. 13 is wider at its ends, having greater width, or cumulative width, than at its mid-section. The wider ends of resilient member 22a laterally spread the spring biasing force generated by the combination of resilient members 22a and 22b. Resilient member 22b increases thickness, and thus resiliency, of resilient member structure 22.

FIG. 14 illustrates a method of fabricating a plurality of a centrally registered, or island-placed, resilient member structure, particularly as seen in FIGS. 13a and 13b. It will be apparent to one of ordinary skill in the art that while the resilient member structures shown in FIGS. 13a and 13b are exemplified, the manufacturing method is applicable to any number of similar resilient member structures.

FIG. 14a illustrates enclosed die cut lines 25' extending through resilient material web 24 to, but not through, its protective release liner, kiss cutting a plurality of spaced apart resilient members 22b. Resilient material web 24 preferably has a layer of adhesive on at least one flat surface side covered by the liner. The resilient material extending around and between the kiss cut resilient members is removed and layered onto a separate protective release liner, 41, as indicated by broken lines, leaving resilient members 22b releasably secured on the original release liner of material web 24. Dashed lines illustrate where the original liner will be slit into a plurality of elongated strips 28a, each strip comprising a plurality of resilient members 22b. Layering the separated resilient material matrix on liner 41 effectively forms a second resilient material web, labeled 24' for clarity.

As a practical matter, resilient material web 24' is the same as resilient material web 24, albeit including a plurality of openings corresponding to the previously kiss cut resilient members 22b. Dashed lines in resilient material web 24' represent where continuous slits 25 will form adjacent rows of elongated resilient material strands 26a, as more particularly illustrated in FIG. 14b. Additionally, dashed lines represent where enclosed die cut lines 25' will form additional resilient members 22c within each strand 26a. The long edges of strands 26a, formed by continuous slits 25, define additional resilient members, 22d, adjacent the openings left by resilient members 22b.

FIG. 14b illustrates elongated resilient material strands 26a kiss cut and removed from release liner 41, of resilient material web 24', as indicated by broken lines. The removed strands 26 are shown slightly spaced apart to indicate that while they were die cut in part along common lines, and thus abut, they are not attached to each other. The removed resilient material strands 26a leave behind a plurality of spaced apart additional resilient members 22c and 22d releasably secured on protective liner 41. Outside waste strand 27 is formed along each long edge thereof, in which some resilient members 22b were previously kiss cut. (Resilient members 22d could conceivably be formed around those openings as well.) Dashed lines in release liner 41 illustrate where the release liner will be slit into elongated strips 28b and 28c, each strip comprising a plurality of resilient members 22c or 22d, respectively, as more particularly illustrated in FIG. 14d.

Figure 14C:
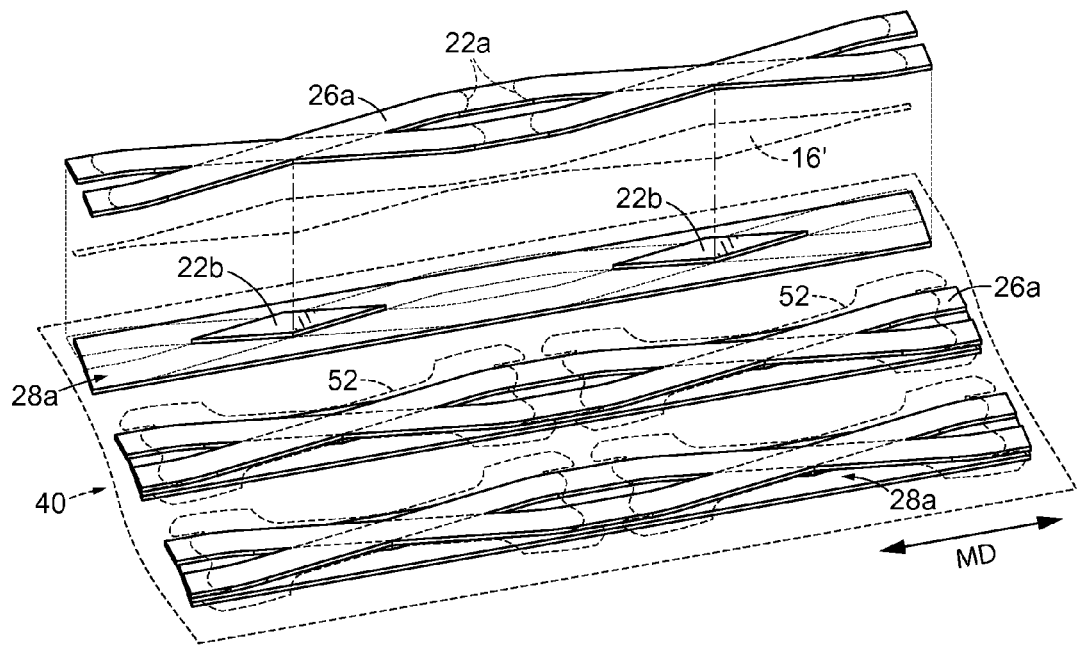

FIGS. 14a-14c show resilient material strand 26a comprising a plurality of successive interconnected resilient members 22a. Resilient member 22b is formed in resilient material web 24 immediately adjacent the mid-section of each interconnected resilient member 22a. As a result, the spaced apart resilient members 22b and the portions of strands 26a corresponding to finished resilient members 22a are effectively pre-registered to each other longitudinally, center to center. The process also renders resilient members 22c and 22d spaced longitudinally equidistant, and thus pre-registered to each other.

Turning now to FIG. 14c, each resilient material strand 26a is overlaid onto elongated strip 28a so that each resilient member 22b is aligned with each interconnected resilient member 22a, as indicated by broken lines and dashed shadow lines. The overlaid resilient members may be secured to each other by use of intermediate layer material web, 16', also represented by dashed lines (and from which intermediate layer 16, interposed between resilient members as described hereinbefore, would be formed). The overlaid resilient members may be combined with at least one additional material web to form laminate 40 from which finished dilators are die cut, as represented by dashed lines. Die cut lines 52 form finished dilators, severing strands 26a into individual resilient members 22a in the process.

Figure 14D:
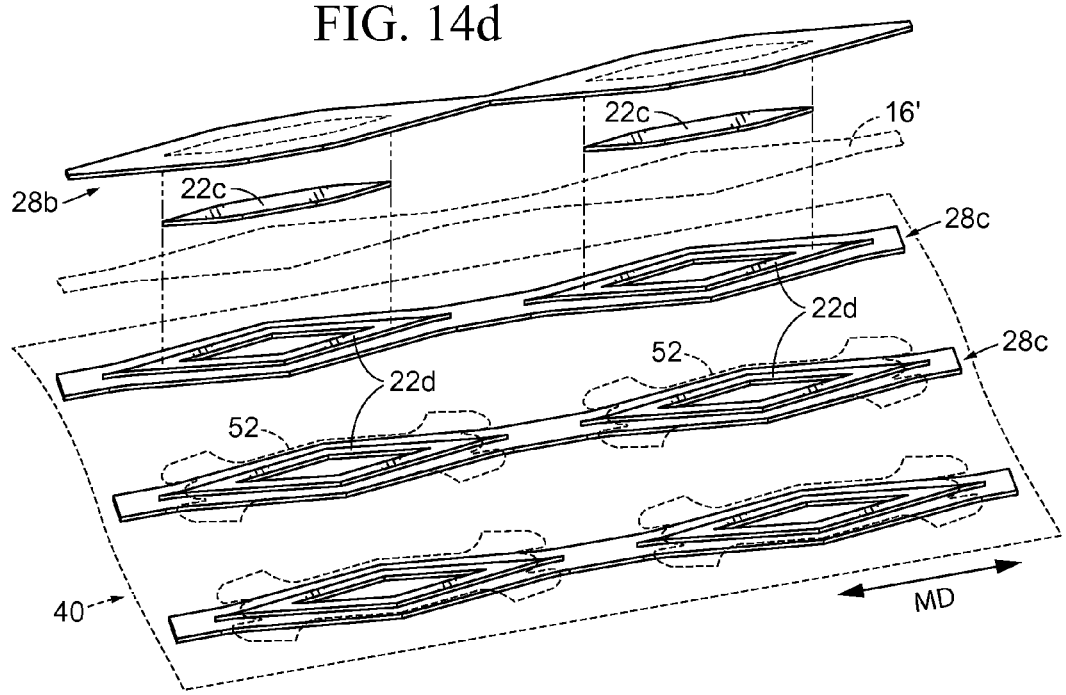

Similarly, FIG. 14d shows elongated strips 28b and 28c, which comprise additional resilient members 22c and 22d, respectively, overlaid and aligned to each other, as indicated by broken lines. One strip must be flipped over so that the respective resilient members from both strips face each other. Again, resilient members 22c and 22d were pre-registered to each other longitudinally, center to center, when die cut from resilient material web 24'. And again, the resilient members may be secured to each other by use of intermediate layer material web 16'.

The overlaid resilient members are combined with at least one additional material web to form laminate 40 from which finished dilators are die cut, as represented by dashed lines. Die cut lines 52 extend outboard the periphery of the overlaid resilient members, but preferably sever, or 'round off' the pointed ends of resilient members 22d in the process. The overlaid resilient members are otherwise substantially island-placed within the peripheral edges of each finished dilator device.

FIG. 15 shows a sixth form of nasal dilator in accordance with the present invention. Arcuate resilient members 22a and 22b overlap along a portion of their respective mid-sections. Non-overlap surface areas define spring finger components extending outward from a common center, defined by overlap surface area 20, to discrete engagement contact points. Overlap surface area 20 has curved long edges and a gradiently reduced width from its mid-section to each end. The radial curvature of one resilient member may be the same, lesser, or greater than the other. The long edges of dilator 10, including the long edges of upper and lower tab extensions 35, generally follow the curvature of the resilient members.

FIG. 15 further illustrates that one resilient member may be longer than the other member. In the present embodiment, resilient member 22b is longer than resilient member 22a, and thus lower tab extensions 35 extend slightly beyond the upper tab extensions 35. The truss's end edge elements generally follow an inward angle, as indicated by broken lines, to better correspond to shape of the nose. If both resilient members are the same width and thickness, spring biasing forces would be correspondingly greater along the upper long half of the device. (Spring biasing forces may be equalized by having the shorter resilient member correspondingly narrower or thinner.) At each end edge 33, terminal end portions 23 correspond to respective protrusions 12, with valley 21 therebetween. Protrusions 12 are preferably separated from tab extensions 35 by a material separation formed therebetween, as described hereinbefore.

Dilator 10 also features a distinct lateral separation between upper and lower discrete contact points, and also between the truss width along lateral centerline b and the lateral separation between upper and lower tab extensions 35. A narrower intermediate region means less potentially irritating adhesive engagement surface area across the bridge of the nose, the skin thereat less likely to be irritated upon removal of the device. (For some people the skin across the bridge of the nose is more sensitive to removal of adhesively attached medical devices. Minimizing device surface area or adhesive contact thereat can thus make a device more comfortable.)

The lateral separation between tab extensions, or the lateral extent d, of dilator 10, spreads spring biasing forces to a greater surface area of the nasal outer wall tissues. The extent of lateral separation between upper and lower contact points, roughly center-to-center, is about 2.7 times greater than the width of overlap surface area 20; the lateral extent d of dilator 10 is about six times greater than the width of overlap surface area 20, and about 3.7 times greater than the width of intermediate region 36 at its narrowest point, at lateral centerline b. At the same time, the length, or longitudinal extent, of overlap surface area 20 is substantial, relative to the overall length of the truss, being equal to about 60% thereof.

FIG. 16 illustrates a seventh form of nasal dilator in accordance with the present invention, illustrating an overlaid resilient member structure alternative to the overlapping resilient member structure seen in FIG. 15. The overall configuration of overlap and non-overlap surface areas, and the resilient properties of the respective resilient member structures of one embodiment are effectively, or alternatively, re-created in the other. Respective resilient member thickness being equal, the resilient member structure of FIGS. 15 and 16 will have similar spring biasing properties. Both structures and their corresponding engagement elements may be efficiently converted into dilator devices using methods substantially as described herein.

Resilient member 22a of FIG. 16 has a peripheral outline at least similar, if not identical, to the periphery of combined overlapped resilient members 22a and 22b as seen in FIG. 15. Resilient member 22a is formed to include spring finger components 22' curving outward from a common center to discrete engagement contact points, as described hereinbefore. Resilient member 22a may also be viewed as including a material separation in the form of a roughly triangular shaped opening extending inward from each end edge. The opening defines the inside long edges of the spring finger components and the lateral separation between upper and lower discrete contact points. Resilient member 22b having substantially the shape of overlap surface area 20 as seen in FIG. 15, is overlaid so as to be centrally registered with, or island-placed onto, resilient member 22a.

FIG. 17 illustrates a eighth form of nasal dilator in accordance with the present invention. Resilient member 22b, having a substantially rectangular mid-section and divergent end portions, overlaps substantially rectangular resilient member 22a such that non-overlap surface areas define spring finger components extending outward from a common center, defined by overlap surface area 20, to discrete engagement contact points. Overlap surface area 20 is thus shaped generally as a trapezoid or four-sided polygon. Resilient member 22b may be configured so that its divergent end portions extend slightly beyond terminal ends 23 of resilient member 22a. FIG. 17d illustrates that dilator 10 may be optionally positioned on the nose with the divergent end portions angled upward so as to engage tissues at or near where the nose meets the cheek, as indicated by a broken line.

FIG. 18 illustrates a ninth form of nasal dilator in accordance with the present invention, illustrating an overlaid/island-placed resilient member structure alternative to the overlapping resilient member structure seen in FIG. 17. The overall configuration of overlap and non-overlap surface areas, and the resilient properties of the respective resilient member structures of one embodiment are effectively, or alternatively, re-created in the other.

Resilient member 22a of FIG. 18 has a peripheral outline at least similar, if not identical, to the periphery of the combined overlapped resilient members 22a and 22b of FIG. 17, including spring finger components 22' that diverge at an oblique angle and extend to discrete engagement contact points. Resilient member 22a may also be viewed as including a material separation in the form of a roughly triangular shaped opening extending inward from each end edge. The opening defines the inside long edges of the spring finger components and the lateral separation between upper and lower discrete contact points. Resilient member 22b, having substantially the shape and position as overlap surface area 20 seen in FIG. 17b, is overlaid and centrally registered with, or island-placed onto, resilient member 22a. Respective resilient member thickness being equal, the resilient member structure of FIGS. 17 and 18 will have similar spring biasing properties. Both dilator devices may be efficiently converted using methods substantially as described herein.

As discussed previously, the intermediate region of dilator 10 is narrower than the lateral separation of resilient member terminal ends 23. In FIGS. 17 and 18 the width of the lateral separation between upper and lower contact points, roughly center-to-center, is about 2.6 times greater than the width of overlap surface area 20; the overall width of dilator 10 is about 5.5 times greater than the width of overlap surface area 20 and about 3.8 times greater than the width of intermediate region 36. The longitudinal extent of overlap surface area 20 in FIG. 17 or resilient member 22b of FIG. 18 is about 64% of the resilient member structure's overall length.

Figure 19A:
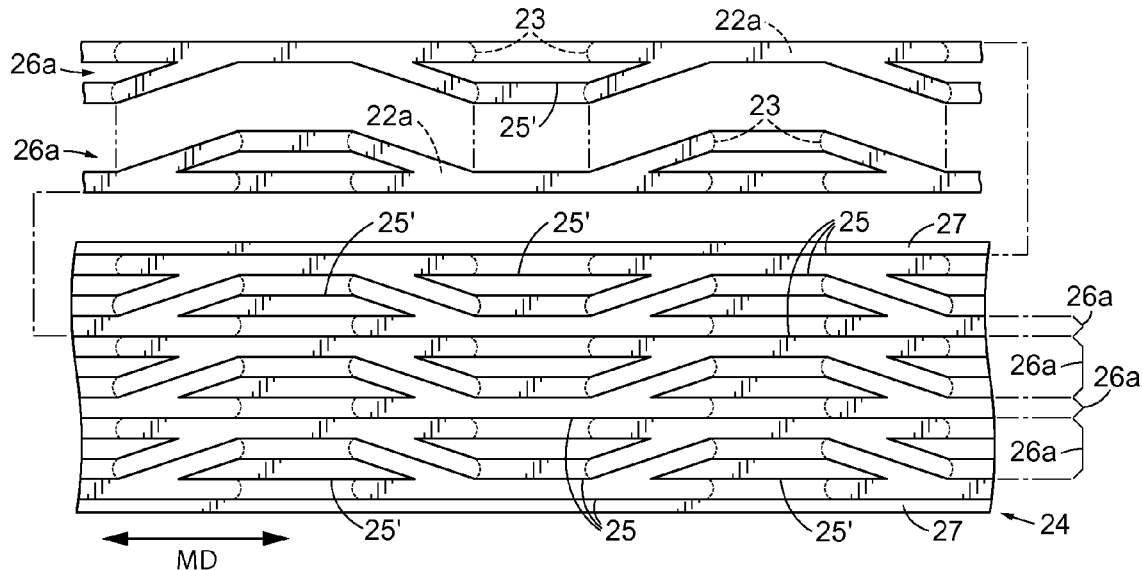
FIGS. 19a and 19b are plan views of a fifth form of manufacturing method in accordance with the present invention by which to fabricate individual resilient members comprising resilient member structures particularly illustrated in FIG. 18.

FIG. 19 illustrates a method of fabricating resilient members 22a and 22b, particularly as seen in FIG. 18, concurrently from resilient material web 24. Web 24 preferably includes a layer of adhesive disposed on one flat surface side covered by a removable protective release liner. FIG. 19a shows that a plurality of continuous slits 25 form adjacent rows of resilient member strands 26a. Enclosed die cut lines 25' are positioned in between slits 25 so as to form a plurality of successive spaced apart resilient members 22b within each strand 26a. Each outside edge of web 24 may include outside waste strand 27.

FIG. 19a further illustrates that the long edges of resilient material strand 26a correspond to the long edges of a plurality of successive interconnected resilient members 22a; dashed lines represent terminal ends 23 thereof. Strand 26a, and thus resilient members 22a and 22b, are configured so that their long edges nest along common die cut lines formed by continuous slits 25 and enclosed die cut lines 25'. Broken lines at the top of FIG. 19a indicate how a pair of strands 26a nest together. Rows of two nested strands also abut along common die cut lines formed by slits 25.

Figure 19B:
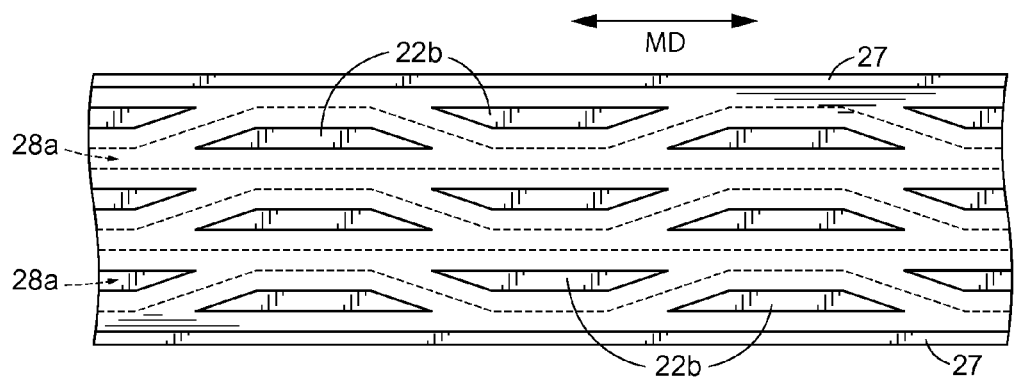
Figure 19C:
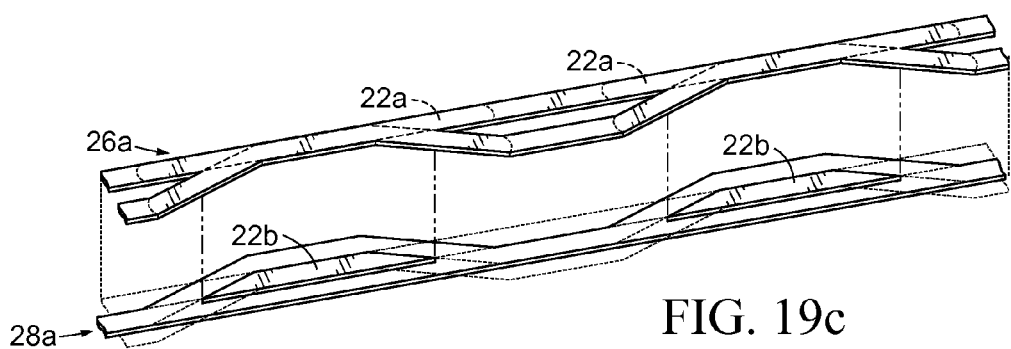
FIG. 19c is an exploded perspective view of the fifth manufacturing method.

FIG. 19b illustrates resilient material strands 26a separated from the protective liner of resilient material web 24, leaving a plurality of spaced apart resilient members 22b thereon. Dashed lines illustrate where the release liner will be slit into a plurality of elongated strips 28a, each strip comprising a plurality of resilient members 22b, as more clearly seen in FIG. 19c. Again, strand 26a and resilient members 22a and 22b are configured so that elongated strip 28a aligns with resilient material strand 26a such that resilient members 22b are centrally registered, or island-placed onto resilient members 22a, as indicated by broken lines and dashed shadow lines in FIG. 19c.

Overlaid resilient material strands 26a and elongated strips 28a may be combined with at least one additional material web corresponding to at least one additional layer of the dilator to form a fabrication laminate as described hereinbefore. Die cut lines extend vertically through the fabrication laminate, forming finished dilator devices and severing strands 26a in the process.

Figure 20D:
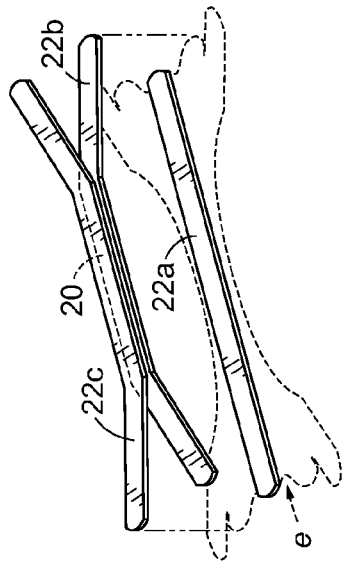
FIGS. 20d, 21d and 22d are exploded perspective views highlighting the resilient member structures of the nasal dilators illustrated in FIGS. 20a, 21a, and 22a, respectively.
Figure 21D:
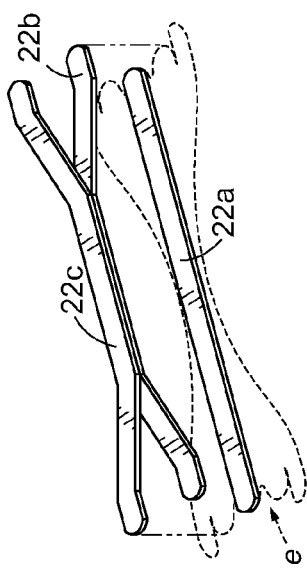

FIGS. 20-22 illustrate three examples, from myriad possible, of a tenth form of nasal dilator in accordance with the present invention. The approximate form of dilator 10 as seen in FIG. 17 is essentially duplicated and flipped laterally, making two parts as the mirror image of each other, each part representing one long half of a single unit. Thus resilient members 22b and 22c, formed to include divergent end portions, overlap rectangular resilient member 22a to create non-overlap surface areas formed as spring finger components extending outward from a common center, defined by overlap surface area 20, to discrete engagement contact points. The drawing figures are arranged to facilitate comparative analysis of the examples given, particularly the resilient member structures thereof.

Figure 22D:
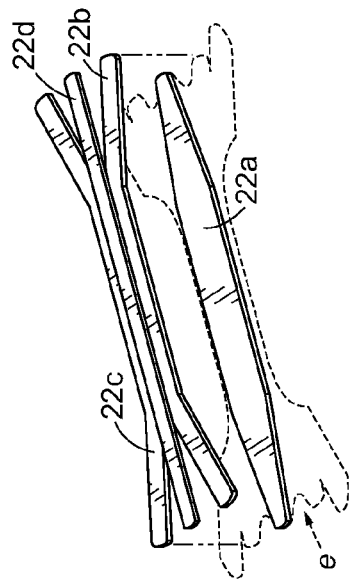

Resilient members 22b and 22c may have the same or similar shape as each other. Their rectangular mid-sections may abut, may be adjacent, spaced apart, or overlap. The divergent end portions of each resilient member are on the same long side of resilient member 22a, and thus the resilient members overlap but do not cross. The resilient members may optionally overlap and cross, as described hereinbefore, particularly with regard to FIG. 10b. The divergent end portions may diverge at the same, or similar, oblique angle. Resilient member 22c is generally rectangular, but may have gradiently tapered end portions as seen in FIG. 22. A fourth, substantially rectangular, resilient member, 22d, may be optionally added to the resilient member structure as illustrated in FIGS. 22b and 22d. The resilient members preferably have a single, constant thickness, however each individual resilient member may be the same or different thickness than any other resilient member.

Figure 20C:
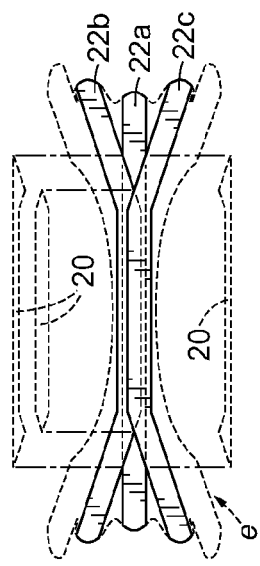
FIGS. 20c, 21c, and 22c are plan views highlighting the resilient member structures of the dilators illustrated in FIGS. 20a, 21a, and 22a, respectively.
Figure 21C:
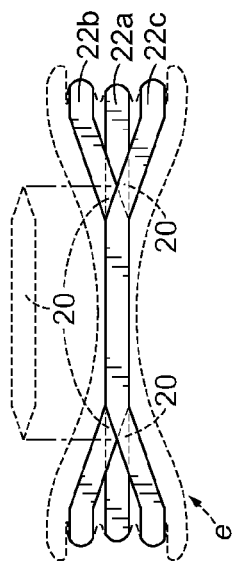
Figure 22C:
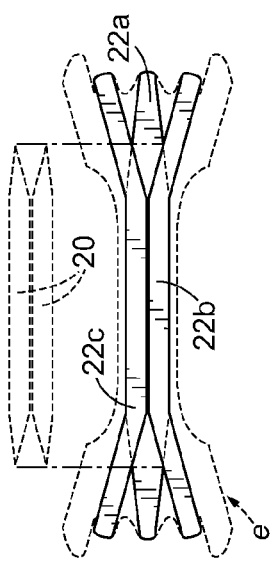

Overlap surface areas 20 are more particularly illustrated in FIGS. 20c, 21c and 22c. FIG. 20c shows overlap surface area 20 along each side of the longitudinal centerline of the truss, having a combined thickness of two resilient members (22c plus 22*a*, and 22*b* plus 22*a*, respectively). A third overlap surface area 20, also indicated in FIG. 20*d*, is formed by the combined thickness of all three resilient members. As seen in FIG. 22*d*, an optional fourth resilient member, 22*d*, may overlap the seam where a long edge from each of adjacent resilient members 22*b* and 22*c* abut. An overlap surface area having a combined thickness of three resilient members, not shown, thus corresponds to the width of resilient member 22*d* extending along said seam.

By virtue of the resilient member structures' divergent end portions, there is a distinct lateral separation between discrete contact points defined by upper and lower resilient member terminal ends 23. Overlap surface areas 20 are from about two to five times narrower than the lateral separation of the outermost contact points, and from about three to six times narrower than the lateral extent of each dilator end region. The length of overlap surface areas 20 range from about 50% to about 64% of the total length of the truss.

FIGS. 23-25 illustrate examples, from myriad possible, of an eleventh form of nasal dilator in accordance with the present invention. Dilator 10 has substantially parallel long edges from end to end, the resilient member structures having substantially rectangular peripheries and parallel long edges. However, individual resilient members 22*a* and 22*b* are irregularly shaped, being wider at their mid-sections and narrower at each terminal end. The drawing figures are arranged so as to facilitate comparative analysis of FIGS. 23, 24 and 25 to each other.

Resilient members 22*a* and 22*b* may be configured to overlap and cross, or alternatively, to overlap without crossing, as described hereinbefore. In either case, overlap surface area 20 extends at least along intermediate region 36, the resilient members having wider mid-sections that taper to narrower ends defined by terminal ends 23. Accordingly, the non-overlap surface areas comprise comparatively shorter spring finger components extending horizontally outward from the common center defined by overlap surface area 20.

As seen in FIG. 23, resilient members 22*a* and 22*b* are configured to form overlap surface area 20 as a diamond or rhombus shape with a gradiently reduced width extending horizontally outward from lateral centerline b. Upper and lower spring finger components, as defined by non-overlap surface areas, extend horizontally outward from the tapered upper and lower long edges of overlap surface area 20.

FIG. 24 shows that resilient members 22*a* and 22*b* overlap along a portion of the width of their respective elongated mid-sections. Overlap surface area 20 is thus formed as a relatively narrow band extending substantially from one truss end region to the other. This resilient member structure approximates that of two substantially parallel resilient member bands positioned adjacent one another and overlaid by a third, island-placed or centrally registered resilient member (an alternative configuration as illustrated substantially in FIG. 27*a* to follow).

FIG. 25 illustrates resilient members 22*a* and 22*b* configured to form overlap surface area 20 as a six-sided polygon. The entire width of the resilient members' elongated mid-sections overlap. The comparatively shorter tapered edges of overlap surface area 20 are positioned roughly at the intersection of intermediate region 36 and respective end regions 32 and 34. FIG. 25 also illustrates a third resilient member 22*c* that forms an additional overlap surface area 20 equal to the combined thickness of all three resilient members. There are thus two overlap surface areas 20 having a second thickness, plus a centrally registered overlap surface area 20 having a third thickness (non-overlap surface areas being a first thickness, assuming all resilient members are equal thickness, as discussed hereinbefore).

Figure 26A:
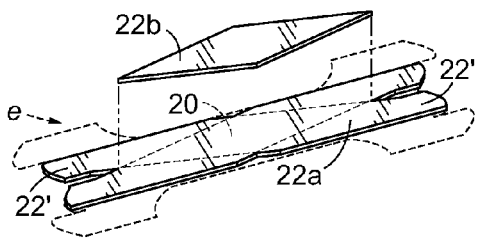
FIGS. 26a, 26b, 26c and 26d are exploded perspective views of a twelfth form of nasal dilator in accordance with the present invention, highlighting the resilient member structures thereof.
Figure 26B:
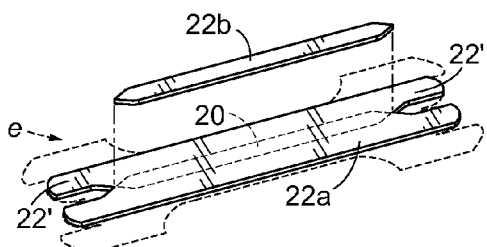
Figure 27A:
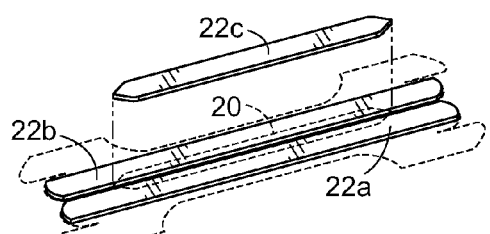
FIGS. 27a and 27b are exploded perspective views of a thirteenth form of nasal dilator in accordance with the present invention, highlighting the resilient member structures thereof.
Figure 27B:
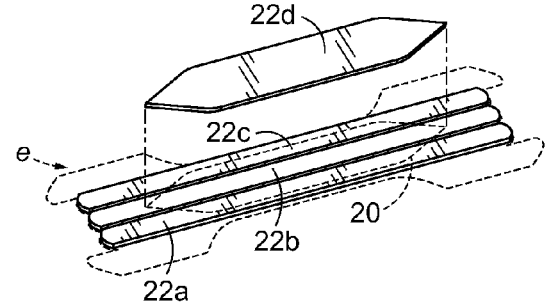

FIGS. 26-27 illustrate twelfth and thirteenth forms of a nasal dilator, respectively, in accordance with the present invention, illustrating island-placed resilient member structures as alternatives to the overlapping resilient member structures seen in FIGS. 23-25. In particular, FIG. 23 corresponds to FIG. 26*a*, FIG. 24 corresponds to FIG. 26*b*, and FIG. 25 corresponds to FIGS. 26*c*/26*d*. FIGS. 27*a* and 27*b* illustrate resilient member structures as a further alternative to those shown in FIGS. 26*b* and 26*c*/26*d*, respectively. Comparisons of similarities and differences between respective resilient member structures may also be made between FIGS. 26*a* and 26*b*; between FIGS. 26*b* and 27*a*; between FIGS. 27*a* and 27*b*, and between FIGS. 26*c* and 27*b*.

The peripheral outlines of resilient members 22*a* seen in FIG. 26 are at least similar, if not identical, to the respective peripheries of combined overlapped resilient members 22*a* and 22*b* as seen in FIGS. 23-24, or resilient members 22*a*, 22*b* and 22*c* as seen in FIG. 25. Resilient members 22*a* as shown in FIG. 26 have parallel long edges and a generally rectangular shape. A material separation in the form of a notch or elongated opening extends inward from each end edge of the resilient member, defining the interior long edges of, and lateral spacing between, the spring finger components adjacent thereto. In FIG. 26*d*, the lateral separation is wide enough to encompass the width of resilient member 22*c*.

Resilient member 22*b*, having substantially the shape and position of overlap surface areas 20 as seen in FIGS. 23-25, is centrally registered, or island-placed, onto resilient member 22*a*. The resilient member structures of FIGS. 26*c* and 26*d* include a third, substantially rectangular resilient member 22*c* positioned substantially along centerline a; in FIG. 26*c*, it extends along the intermediate region of the truss, and in FIG. 26*d* extends the length of the truss. (The dilator device of FIG. 26*c* is somewhat similar to that discussed previously with regard to FIG. 7.)

Figure 26C:
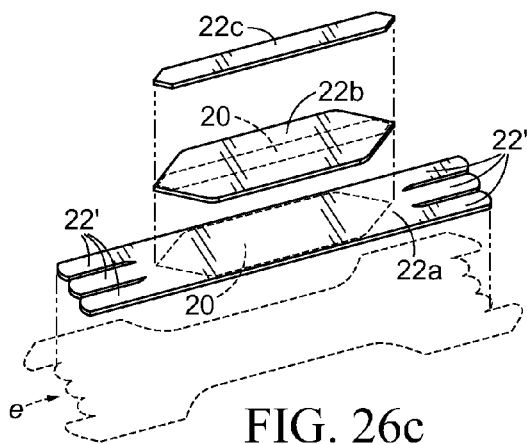
Figure 26D:
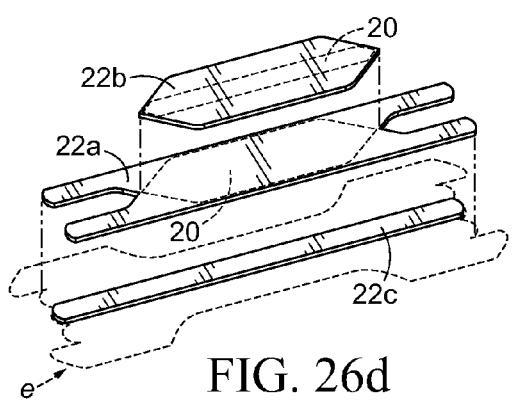

FIGS. 27*a* and 27*b* illustrate further alternative resilient member structures to those shown in FIGS. 26*b* and 26*c*/26*d*, respectively. At least one island-placed or centrally registered resilient member, 22*c* or 22*d*, overlays two or three substantially parallel adjacent resilient members. The width of the overlaid resilient member straddles at least one longitudinal space between the inside long edges of at least two parallel resilient members. An island-placed resilient member overlaid in this manner may be of any shape preferably confined to within the peripheral outline of the resilient member structure as a whole.

As illustrated and described, the dilator devices of resilient member structures of FIGS. 23-25 have similar spring biasing properties compared to the corresponding alternative resilient member structures of FIGS. 26 and 27, respective resilient member thickness being equal. Both sets of resilient member structures and their corresponding engagement elements may be efficiently converted into dilator devices using methods substantially as described herein.

FIGS. 28 and 29 illustrate a fourteenth form of nasal dilator in accordance with the present invention. Resilient member 22*a* is formed to include spring finger components 22' extending outward from a common center at its mid-section to discrete engagement contact points at each end region of the truss. Resilient member 22*a* may also be viewed as generally rectangular and including a material separation in the form of an elongated opening extending inward from each end edge. The material separation bifurcates resilient member 22*a*, defining the inside long edges of the spring finger components and the lateral separation between upper and lower discrete contact points.

The spring finger components may have a constant or tapered width, they may be parallel to each other or diverge, or they may be uniform or asymmetric. The common center extends horizontally along at least a portion of the intermediate region of the truss, overlaid by resilient member 22b thereat. Terminal ends 23 of resilient member 22b may extend longitudinally to, past, or alternatively, short of, terminal ends 23 of spring finger components 22'. Similarly, terminal ends 23 of either resilient member 22a or 22b may extend to the lateral end edges of the truss, or alternatively, extend short thereof. The width of resilient member 22b at its mid-section preferably corresponds to the lateral spacing between upper and lower spring finger components.

Figure 30B:
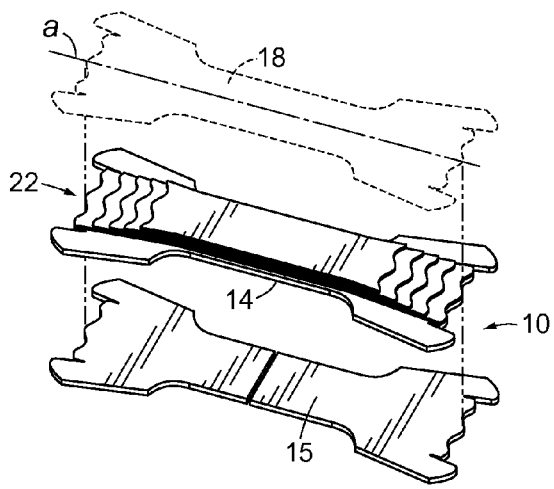
Figure 30A:
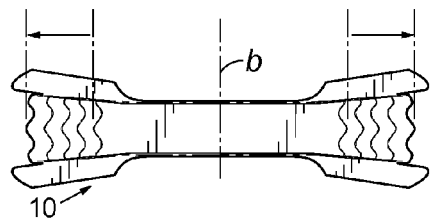
FIG. 30a is a plan view of a fifteenth form of nasal dilator in accordance with the present invention.
Figure 31C:
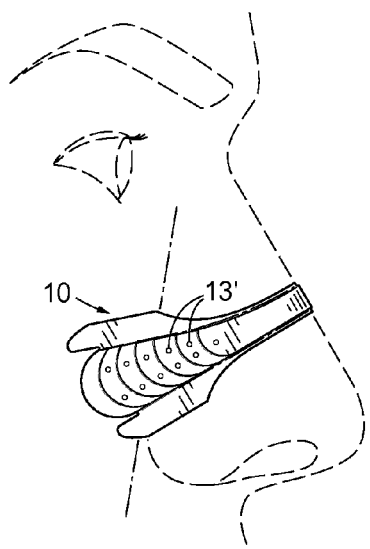
FIG. 31c is a side elevation showing the attachment of the nasal dilator of FIG. 31a to the nose of a wearer depicted in broken lines.
Figure 31B:
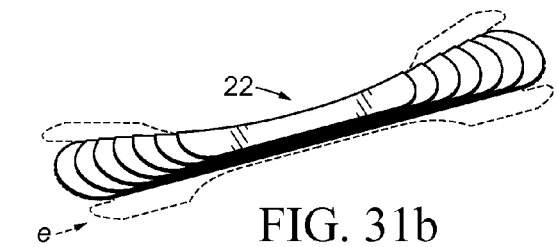

FIGS. 30-32 illustrate examples, from myriad possible, of a fifteenth form of nasal dilator in accordance with the present invention. Resilient member structure 22 comprises a plurality thin resilient members of progressively less length arranged in a leaf spring manner, creating a stepped reduction from greater to lesser thickness. The cumulative resiliency of the stacked resilient member mid-sections extends longitudinally outward from lateral centerline b to where it is reduced along the length of the successive steps at each end region, as indicated by directional arrows. The number of steps corresponds to the number of overlaid resilient members. (Note that a stepped reduction in thickness extending laterally outward from longitudinal centerline a was discussed previously with respect to FIG. 2.)

The stepped reduction in resilient member structure thickness creates a corresponding stepped reduction in resiliency, a designed directional element of dilator 10, whereby to decrease spring biasing peel forces at the end regions of the truss, particularly in view of the resilient member structure's engineered spring constant as compared to that of a single member resilient structure (or two closely parallel resilient members). Individual resilient members preferably have the same thickness. However, to add a further dynamic element, some or all resilient members may be of greater or lesser thickness.

To generate a suitable range of spring biasing force, a single resilient member (or two adjacent, parallel, resilient members) have a length, a width, and a constant thickness along said length. To generate the same, similar, or greater range of spring biasing force, the plurality of stacked resilient members comprising the leaf spring structure may have the same or similar width as the single or two parallel members, but only a proportional fraction of thickness. Determining said proportional fraction of thickness should take into account the corresponding increase in resiliency for each stepped reduction in length, any compounding effect created by virtue of there being a plurality of stacked or overlaid members, and the maximum spring constant that may be generated given the reduction thereof at each end region.

FIGS. 30 and 31 particularly illustrate that resilient member structure 22 has enlarged end portions, formed by tapered long edges of the constituent resilient members in FIG. 30, and by the radial curvature of one long edge of each resilient member in FIG. 31, the latter of which serves to spread spring biasing both laterally and away from longitudinal centerline a, roughly at an oblique angle thereto as indicated by broken lines. FIG. 31c illustrates dilator 10 positioned on the nose with the divergent portion of the end regions positioned up, so as to engage tissues at or near where the nose meets the cheek as indicated by a broken line. Alternatively, the device may be positioned on the nose with the divergent portion down, extending over the nostril or nasal vestibule.

Figure 31A:
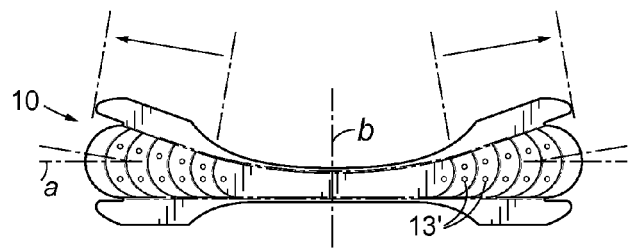
FIG. 31a is a plan view of a variation of the nasal dilator of FIG. 30.

FIGS. 31a and 31c also illustrates that resilient member structure 22 may optionally include a plurality of small interior material separations in the form of openings, 13', positioned so as to selectively reduce resiliency. Openings may extend vertically through all layers of the dilator so as to make the device more breathable by allowing moisture vapor to pass vertically through the openings, away from the skin.

Figure 32A:
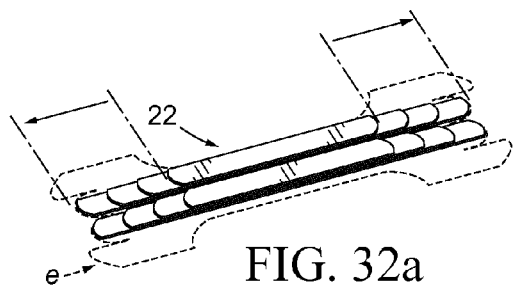
FIGS. 32a and 32b are perspective views highlighting the resilient member structure of a variation of the nasal dilator of FIG. 30.
Figure 32B:
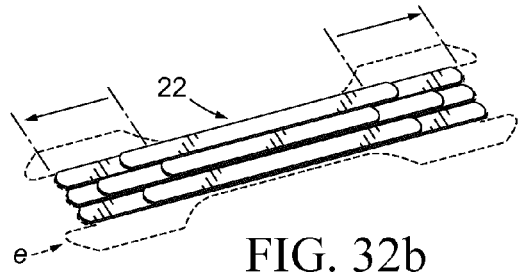

FIG. 32 illustrates a leaf spring structure applied to two, or alternatively, three, adjacent, substantially rectangular, parallel resilient members. FIG. 32a illustrates an even and symmetric stepped reduction in length; FIG. 32b illustrates that the stepped reduction in length, and the number of constituent resilient members thereof, may vary.

The stepped reduction in thickness preferably extends along the respective end regions of the truss, as indicated approximately by broken lines in FIGS. 30-32, but may optionally extent into the intermediate region. The progressive reduction in length may be uniform or disparate, in either or both end regions. It will be apparent to one of ordinary skill in the art that resilient member structure 22 of FIGS. 30-32 is roughly analogous to, or otherwise an alternative to, a single resilient member being sculpted or formed so as to have the same or similar vertical profile of stepped, reduced thickness.

FIGS. 33 and 34 illustrate a sixteenth form of nasal dilator in accordance with the present invention. The previously described stepped reduction in resilient member thickness and corresponding reduction in resiliency is spread both laterally across the width, and horizontally along the length, of each end region of the truss. FIG. 33 illustrates resilient member structure 22 having at least one substantially rectangular resilient member overlaid by a plurality of resilient members having a substantially rectangular mid-section and divergent end portions. FIG. 34 illustrates resilient member structure 22 having identical resilient members progressively offset relative to longitudinal centerline a and/or lateral centerline b in a staggered overlapping relationship. The constituent resilient members of either resilient member structure 22 may be stacked in any order. Individual resilient members preferably have the same thickness. However, to add a further dynamic element, some or all resilient members may be of greater or lesser thickness.

Figure 33A:
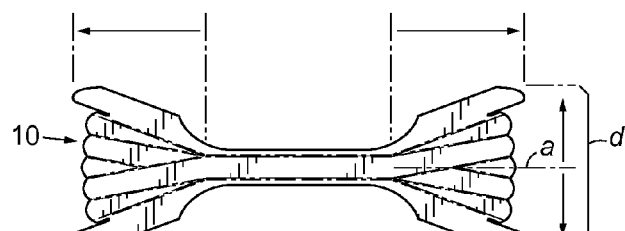
FIG. 33a is a plan view of a sixteenth form of nasal dilator in accordance with the present invention.
Figure 33B:
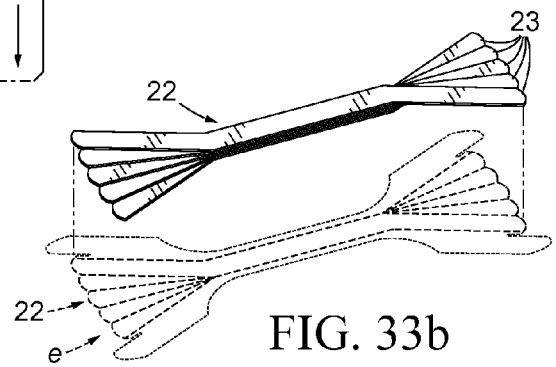

FIG. 33 further illustrates individual resilient members having divergent end portions that overlap and cross, as described hereinbefore. Their mid-sections are substantially overlaid and their divergent end portions are on opposite sides of longitudinal centerline a. The divergent end portions may optionally be on the same side of longitudinal centerline a, also as described hereinbefore, without departing from the intended configuration of resilient member structure 22. In either case, the angle at which the end portions diverge from the mid-section is varied and stepped in a fanfold-like manner so that the cumulative resiliency of the stacked resilient member mid-sections is spread substantially across the end regions of the truss, as indicated by directional arrows extending laterally from longitudinal centerline a. FIG. 33b particularly illustrates the preferred stepped fanfold stacking order. Alternatively, FIG. 33a illustrates the substantially rectangular resilient member positioned at the bottom of the stacking order.

Figure 34A:
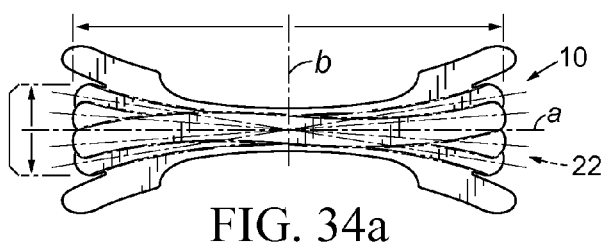
FIG. 34a is a plan view of a variation of the nasal dilator of FIG. 33.

The end portions of the individual resilient members illustrated in FIG. 34 have an identical, but reversed, curvature on either side of lateral centerline b. Half of the resilient members are flipped laterally from the other half, preferably a pair of which are laterally and longitudinally aligned with the truss. At least one additional pair of resilient members are rotated slightly relative thereto. By virtue of the resilient member curvature, as well as being flipped laterally, and the slight rotation of at least some of the resilient members, terminal ends 23 thereof are progressively offset relative to longitudinal centerline a, as indicated by broken lines in FIG. 34a. This creates a stepped reduction in thickness extending primarily laterally, at each end regions, and very slightly arcuately, from longitudinal centerline a.

Figure 34B:
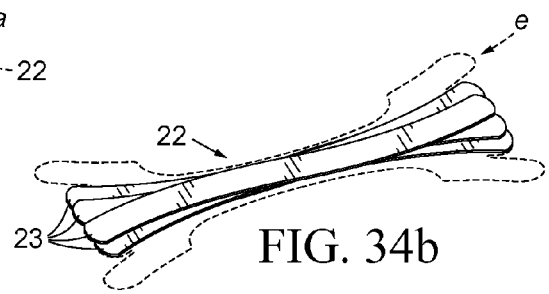

This spatial arrangement of resilient members means that their respective mid-sections are not precisely overlaid, and the width of the resilient member structure thereat is not perfectly uniform. However, the cumulative resiliency of the stacked resilient member mid-sections is primarily imparted to the offset end portions and spread laterally across the end regions of the truss. To a lesser extent, the cumulative resiliency generated at lateral centerline b is spread along the gradually increasing width of resilient member structure 22 extending horizontally outward from lateral centerline b to the opposite end edges of the truss as indicated by directional arrows. FIG. 34b more particularly illustrates the preferred stacking order of the constituent resilient members.

As illustrated and described in examples of the preferred embodiments, the present invention provides medical devices for dilating external tissue, including a wide range of nasal dilator devices having complex resilient member structures, including methods of fabricating the constituent members of said structures and corresponding finished nasal dilator devices.

I claim:

1. A nasal dilator comprising:
   a resilient member structure comprising a plurality of resilient members, each resilient member extending at least substantially from one end of the nasal dilator to another end of the nasal dilator,
   each resilient member including a substantially rectangular mid-section, at least one resilient member including at least one divergent portion diverging obliquely from the mid-section, wherein
   at least one resilient member has a greater thickness than at least one other resilient member, and
   at least two resilient members overlap along at least a substantial portion of their mid-sections such that long edges of the mid-sections are substantially parallel to each other, the mid-section long edges substantially parallel to a longitudinal centerline of the dilator, and the at least one divergent portion of the at least one resilient member and another end portion of a different resilient member forming adjacent spring fingers extending into a same end region of the nasal dilator.

2. The nasal dilator of claim 1 wherein the at least two resilient members overlapping along a substantial portion of their respective mid-sections include a divergent portion diverging obliquely from each end of the resilient member mid-section, one divergent portion diverging to one side of the longitudinal centerline of the dilator, an opposite divergent portion diverging to an opposite side of said longitudinal centerline.

3. The nasal dilator of claim 1 wherein the resilient member structure forms the truss in its entirety.

4. The nasal dilator of claim 1, further comprising:
   an engagement element secured to at least a portion of at least one resilient member, the engagement element defining at least a substantial portion of a periphery of the dilator, the engagement element selected from the group consisting of:
   a) a base layer made from a thin, supple plastic film;
   b) a cover layer;
   c) a base layer secured to at least a portion of one flat surface side of the resilient layer and a cover layer secured to at least a portion of an opposite flat surface side of the resilient layer; or
   d) at least one of an intermediate layer, the intermediate layer interposed between two resilient members, the at least one of an intermediate layer dividing the resilient member structure into two or more resilient layers.

5. The nasal dilator of claim 1, further comprising an intermediate layer interposed between two resilient members, the intermediate layer dividing the resilient member structure into at least two resilient layers.

6. The nasal dilator of claim 1, the divergent portion further including a terminal end that defines a terminus of the resilient member, or further comprising a resilient member end portion extending from the divergent portion, said end portion extending substantially parallel to the mid-section, the end portion including a resilient member terminal end.

7. The nasal dilator of claim 1, wherein the resilient member structure is further selected from the group consisting of:
   a) the at least two resilient members overlapping along at least a substantial portion of their mid-sections each include at least one divergent portion extending from the mid-section, the at least one divergent portion of one resilient member diverging to a first side of the longitudinal centerline of the dilator, the at least one divergent portion of the other resilient member diverging to an opposite side of the longitudinal centerline;
   b) the at least two resilient members overlapping along at least a substantial portion of their mid-sections each include a divergent portion extending from each end of the mid-section, the divergent portions of one resilient member diverging to a same side of the longitudinal centerline of the dilator, the divergent portions of the other resilient member diverging to an opposite side of the longitudinal centerline;
   c) the end portions of one resilient member are substantially in line with the mid-section thereof such that the resilient member is substantially straight between opposite terminal ends thereof;
   d) at least one resilient member mid-section has a greater width than at least one end portion thereof; or
   e) a first resilient member having at least one divergent portion extending from the mid-section and diverging to a first side of said longitudinal centerline, a second resilient member being substantially straight from one terminal end to an opposite terminal end, a third resilient member having at least one divergent portion extending from the mid-section and diverging to a second side of said longitudinal centerline, the first and the third resilient members positioned side by side along their mid-sections, laterally adjacent and substantially parallel to each other, the second resilient member overlapping at least one of the first and third resilient members.

8. The nasal dilator of claim 1, wherein:
   the at least two resilient members overlapping along at least a substantial portion of their mid-sections each include a divergent portion diverging obliquely from at least one end of the mid-section, at least some of the divergent portions progressively offset relative to each other such that the spring fingers are staggered or fanned across a width of at least one end region of the dilator.

9. A nasal dilator comprising:
   a resilient member structure having outer long edges extending from a first end region through an intermediate region to a second end region of the dilator, the edges substantially parallel to a longitudinal centerline of the dilator, the resilient member structure including at least two overlapping resilient members extending lengthwise along at least the intermediate region of the dilator;

at least a portion of a flat surface side of at least one resilient member overlapping onto at least a portion of a flat surface side of at least one other resilient member, said overlapping surfaces extending along at least a portion of the intermediate region of the dilator; and wherein the resilient member structure includes at least two laterally adjacent spring finger components extending into one end region of the dilator, one of the two laterally adjacent spring finger components formed by a non-overlap portion of a first resilient member and another of the two laterally adjacent spring fingers formed by a non-overlap portion of a second, different resilient member.

10. The nasal dilator of claim 9 wherein at least one resilient member has a greater thickness than at least one other resilient member.

11. The nasal dilator of claim 9, further comprising:
an engagement element secured to at least a portion of at least one resilient member, the engagement element defining at least a substantial portion of a periphery of the dilator, the engagement element selected from the group consisting of:
a) a base layer made from a thin, supple plastic film;
b) a cover layer;
c) a base layer secured to at least a portion of one flat surface side of the resilient layer and a cover layer secured to at least a portion of an opposite flat surface side of the resilient layer; or
d) at least one of an intermediate layer, the intermediate layer interposed between two resilient members, the at least one of an intermediate layer dividing the resilient member structure into two or more resilient layers.

12. The nasal dilator of claim 9 wherein:
the at least two laterally adjacent spring finger components are at least three laterally adjacent spring finger components, two of the at least three spring finger components formed by the first resilient member and one of the at least three spring finger components formed by the second, different resilient member.

13. The nasal dilator of claim 9 wherein:
at least two laterally adjacent, substantially parallel, oblong resilient members are spaced apart along long edges thereof, the at least one resilient member is substantially parallel thereto and overlaps at least a portion of a width of at least two of said laterally adjacent resilient members; and
end portions and terminal ends of the at least two laterally adjacent resilient members form said laterally adjacent spring finger components.

14. The nasal dilator of claim 9 wherein:
from two to four laterally adjacent, substantially parallel, oblong resilient members are spaced apart along long edges thereof;
a plurality of the at least one resilient member overlays at least a portion of a length of at least one of said laterally adjacent resilient members such that the resilient member structure has a stepped reduction in thickness extending longitudinally from a lateral centerline of the dilator to at least one terminal end of a longest resilient member, the stepped reduction in thickness corresponding to a gradient decrease in resiliency of the resilient member structure; and
end portions and terminal ends of at least two of the laterally adjacent resilient members form said laterally adjacent spring finger components.

15. The nasal dilator of claim 9 wherein:
the at least one resilient member and the at least one other resilient member each have a mid-section wider than at least one end portion thereof; and
the resilient members mid-sections overlap such that two of said at least one end portion form the at least two laterally adjacent spring finger components.

16. A nasal dilator comprising:
a plurality of resilient material strands, each strand extending substantially from one end of the nasal dilator, through an intermediate region of the nasal dilator to an opposite end of the nasal dilator;
a first resilient material strand of the plurality partially overlapping a second resilient material strand of the plurality to form an overlap area having a shape different from either the first resilient material strand or the second resilient material strand, said first material strand having substantially parallel long edges along the overlap area and said second material strand having substantially parallel long edges along the overlap area;
the overlap area extending over the intermediate region of the dilator and horizontally symmetrical about a lateral centerline of the dilator;
at least one non-resilient material layer whose outer edges substantially define a plan view outline of the dilator; and
said plurality of resilient material strands and at least one non-resilient material layer laminated into a structure having a size and an aspect ratio suitable for use across a bridge of a human nose and a spring-biasing force between about 15 grams and about 35 grams.

17. A nasal dilator comprising:
a plurality of resilient material strands, each strand extending substantially from one end of the nasal dilator, through an intermediate region of the nasal dilator to an opposite end of the nasal dilator;
a first resilient material strand of the plurality partially overlapping a second resilient material strand of the plurality to form an overlap area having a shape different from either the first resilient material strand or the second resilient material strand;
the overlap area extending over the intermediate region of the dilator and horizontally symmetrical about a lateral centerline of the dilator;
at least one non-resilient material layer whose outer edges substantially define a plan view outline of the dilator; and
said plurality of resilient material strands and at least one non-resilient material layer laminated into a structure having a size and an aspect ratio suitable for use across a bridge of a human nose and a spring-biasing force between about 15 grams and about 35 grams, wherein the first resilient material strand is asymmetrical about the lateral centerline of the dilator.

18. The nasal dilator of claim 17, wherein a longest perimeter edge of the overlap area is parallel to a horizontal centerline of the dilator.

19. A nasal dilator comprising:
a plurality of resilient material strands, each strand extending substantially from one end of the nasal dilator, through an intermediate region of the nasal dilator to an opposite end of the nasal dilator;
a first resilient material strand of the plurality partially overlapping a second resilient material strand of the plurality to form an overlap area having a shape different from either the first resilient material strand or the second resilient material strand;

the overlap area extending over the intermediate region of the dilator and horizontally symmetrical about a lateral centerline of the dilator;

at least one non-resilient material layer whose outer edges substantially define a plan view outline of the dilator; and said plurality of resilient material strands and at least one non-resilient material layer laminated into a structure having a size and an aspect ratio suitable for use across a bridge of a human nose and a spring-biasing force between about 15 grams and about 35 grams, wherein the first resilient material strand comprises a first segment that is parallel to a horizontal centerline of the dilator, and a second segment that is divergent from the horizontal centerline of the dilator.

20. The nasal dilator of claim 19, wherein the first resilient material strand is symmetrical about the lateral centerline of the dilator.

* * * * *